US011236379B2

(12) United States Patent
Auner et al.

(10) Patent No.: US 11,236,379 B2
(45) Date of Patent: Feb. 1, 2022

(54) RAMAN BASED DETECTION INSTRUMENT AND METHOD OF DETECTION

(71) Applicants: Seraph Biosciences, Inc., Detroit, MI (US); Wayne State University, Detroit, MI (US)

(72) Inventors: Gregory William Auner, Livonia, MI (US); Charles Shanley, Grosse Pointe Farms, MI (US); Michelle Brusatori, Sterling Heights, MI (US); Tara Twomey, Novi, MI (US); David Sant, Wixom, MI (US)

(73) Assignees: Seraph Biosciences, Inc., Detroit, MI (US); Wayne State University, Detroit, MI (US)

( * ) Notice: Subject to any disclaimer, the term of this patent is extended or adjusted under 35 U.S.C. 154(b) by 101 days.

(21) Appl. No.: 16/284,050

(22) Filed: Feb. 25, 2019

(65) Prior Publication Data
US 2019/0203255 A1 Jul. 4, 2019

Related U.S. Application Data

(63) Continuation of application No. 14/910,459, filed as application No. PCT/US2014/050182 on Aug. 7, 2014, now Pat. No. 10,253,346.
(Continued)

(51) Int. Cl.
*C12Q 1/04* (2006.01)
*G01J 3/44* (2006.01)
(Continued)

(52) U.S. Cl.
CPC .............. *C12Q 1/04* (2013.01); *A61B 5/0075* (2013.01); *C12Q 1/14* (2013.01); *G01J 3/0208* (2013.01);
(Continued)

(58) Field of Classification Search
CPC .................................. G01J 3/44; G01N 21/65
See application file for complete search history.

(56) References Cited

U.S. PATENT DOCUMENTS 5,842,995 A * 12/1998 Mahadevan-Jansen ..................... A61B 5/0071 600/473
6,064,897 A 5/2000 Lindberg et al.
(Continued)

FOREIGN PATENT DOCUMENTS

CN 101166957 4/2008
CN 103134788 6/2013
(Continued)

OTHER PUBLICATIONS

Lorna Ashton, "Raman spectroscopy: lighting up the future of microbial identification", 2011 (Year: 2011).*
(Continued)

*Primary Examiner* — Maurice C Smith
(74) *Attorney, Agent, or Firm* — Finnegan, Henderson, Farabow, Garrett & Dunner, LLP

(57) ABSTRACT

A Raman spectroscopy based system and method for examination and interrogation provides a method for rapid and cost effective screening of various protein-based compounds such as bacteria, virus, drugs, and tissue abnormalities. A hand-held spectroscope includes a laser and optical train for generating a Raman-shifting sample signal, signal processing and identification algorithms for signal conditioning and target detection with combinations of ultra-high resolution micro-filters and an imaging detector array to provide specific analysis of target spectral peaks within discrete spectral bands associated with a target pathogen.

17 Claims, 19 Drawing Sheets

Related U.S. Application Data

(60) Provisional application No. 61/863,095, filed on Aug. 7, 2013.

(51) Int. Cl.
    *G01J 3/02*          (2006.01)
    *G01N 21/65*       (2006.01)
    *A61B 5/00*        (2006.01)
    *C12Q 1/14*        (2006.01)

(52) U.S. Cl.
CPC ........... *G01J 3/0264* (2013.01); *G01J 3/0272* (2013.01); *G01J 3/0291* (2013.01); *G01J 3/44* (2013.01); *G01J 3/4406* (2013.01); *G01J 3/4412* (2013.01); *G01N 21/65* (2013.01); *A61B 5/445* (2013.01); *A61B 5/682* (2013.01); *A61B 5/6815* (2013.01); *A61B 5/6819* (2013.01); *A61B 5/6846* (2013.01); *G01N 2201/0221* (2013.01); *G01N 2333/11* (2013.01); *G01N 2333/31* (2013.01); *G01N 2333/34* (2013.01)

(56) References Cited

U.S. PATENT DOCUMENTS

| | | | |
|---|---|---|---|
| 6,069,689 | A | 5/2000 | Zeng et al. |
| 6,396,584 | B1 | 5/2002 | Taguchi et al. |
| 6,587,711 | B1 | 7/2003 | Alfano et al. |
| 7,695,995 | B2 | 4/2010 | Hwang |
| 8,414,473 | B2 | 4/2013 | Jenkins et al. |
| 8,873,041 | B1 | 10/2014 | Chai et al. |
| 2001/0002315 | A1 | 5/2001 | Schultz et al. |
| 2001/0034478 | A1 | 10/2001 | Lambert et al. |
| 2002/0156380 | A1* | 10/2002 | Feld ..................... A61B 5/0075 600/473 |
| 2003/0053049 | A1 | 3/2003 | Fink et al. |
| 2005/0043588 | A1 | 2/2005 | Tsai |
| 2005/0075575 | A1 | 4/2005 | Vo-Dinh |
| 2005/0236554 | A1 | 10/2005 | Fontaine et al. |
| 2005/0248758 | A1* | 11/2005 | Carron ................... G01N 21/65 356/301 |
| 2006/0051252 | A1 | 3/2006 | Yuan et al. |
| 2006/0176478 | A1* | 8/2006 | Clarke .................. G01J 3/0218 356/301 |
| 2006/0250613 | A1 | 11/2006 | Demuth et al. |
| 2006/0268266 | A1 | 11/2006 | Gardner, Jr. et al. |
| 2007/0038120 | A1 | 2/2007 | Richards-Kortum et al. |
| 2007/0153288 | A1 | 7/2007 | Wang et al. |
| 2007/0279627 | A1 | 12/2007 | Tack et al. |
| 2008/0002198 | A1* | 1/2008 | Sun .......................... G01J 3/44 356/301 |
| 2008/0221409 | A1 | 9/2008 | Hoarau |
| 2008/0309931 | A1 | 12/2008 | Silberberg et al. |
| 2009/0082695 | A1 | 3/2009 | Whitehead |
| 2009/0088615 | A1 | 4/2009 | Robinson et al. |
| 2011/0186436 | A1 | 8/2011 | Novosselov et al. |
| 2011/0204258 | A1 | 8/2011 | Heller et al. |
| 2012/0027047 | A1 | 2/2012 | Lane et al. |
| 2012/0035442 | A1 | 2/2012 | Barman |
| 2012/0085900 | A1 | 4/2012 | Verbeck, IV |
| 2012/0089030 | A1 | 4/2012 | Guze et al. |
| 2012/0145906 | A1 | 6/2012 | Treado et al. |
| 2012/0154801 | A1 | 6/2012 | Carron |
| 2012/0182438 | A1 | 7/2012 | Berkner et al. |
| 2012/0281218 | A1 | 11/2012 | Schnitzer et al. |
| 2012/0309080 | A1 | 12/2012 | Cunningham et al. |
| 2013/0052636 | A1 | 2/2013 | Verma et al. |
| 2013/0099249 | A1 | 4/2013 | Forcier et al. |
| 2014/0121508 | A1 | 5/2014 | Latimer et al. |
| 2014/0320858 | A1* | 10/2014 | Goldring ............... G01J 3/0208 356/416 |

FOREIGN PATENT DOCUMENTS

| | | |
|---|---|---|
| CN | 103196888 | 7/2013 |
| EP | 1 469 290 A1 | 10/2004 |
| WO | WO 2006016913 | 2/2006 |
| WO | WO 2006113537 | 10/2006 |

OTHER PUBLICATIONS

Shao-Wei Wang, "Concept of a high-resolution miniature spectrometer using an integrated filter array" 2007 (Year: 2007).*

Pau, J.L. et al., "Plasma-assisted molecular beam epitaxy of nitride-based photodetectors for UV and visible applications", *Journal of Crystal Growth*, 278 (2005), pp. 718-722 (published on line on Feb. 11, 2005).

Rule 71(3) Communication dated Jun. 29, 2020, in European Application No. 14 834 893.1 (68 pages).

Extended European Search Report for EP 3030870 (PCT/US2014/050182), dated Dec. 12, 2017, 22 pages.

International Search Report, International Application No. PCT/US2014/050182, dated Nov. 18, 2014, 1 page.

Neugebauer et al., Towards a Detailed Understanding of Bacterial Metabolism-Spectroscopic Characterization of *Staphylococcus epidermidis*, ChemPhysChem 2007, pp. 124-137, vol. 8., No. 1.

Neugebauer et al., The Influence of Fluoroquinolone Drugs on the Bacterial Growth of S. epidermidis Utilizing the Unique Potential of Vibrational Spectroscopy, *Journal of Physical Chemistry*, Apr. 2007, pp. 2898-2906, vol. 111, No. 15.

Schmidt, Oliver, Integration of chip-size wavelength detectors into optical sensing systems (Doctoral dissertation), University of Erlangen-Nuremberg, 2007, pp. 1-177.

State Intellectual Property Office of People's Republic of China, Application No. 201480044989.4, Jan. 22, 2017, 10 pages.

Utzinger et al., Fiberoptic Probes for Biomedical Optical Spectroscopy, Journal of Biomedical Optics, Jan. 2003, pp. 121-147, vol. 8, No. 1.

Partial European Search Report from EP Application No. 21167040.1, dated Oct. 15, 2021 (16 pages).

* cited by examiner

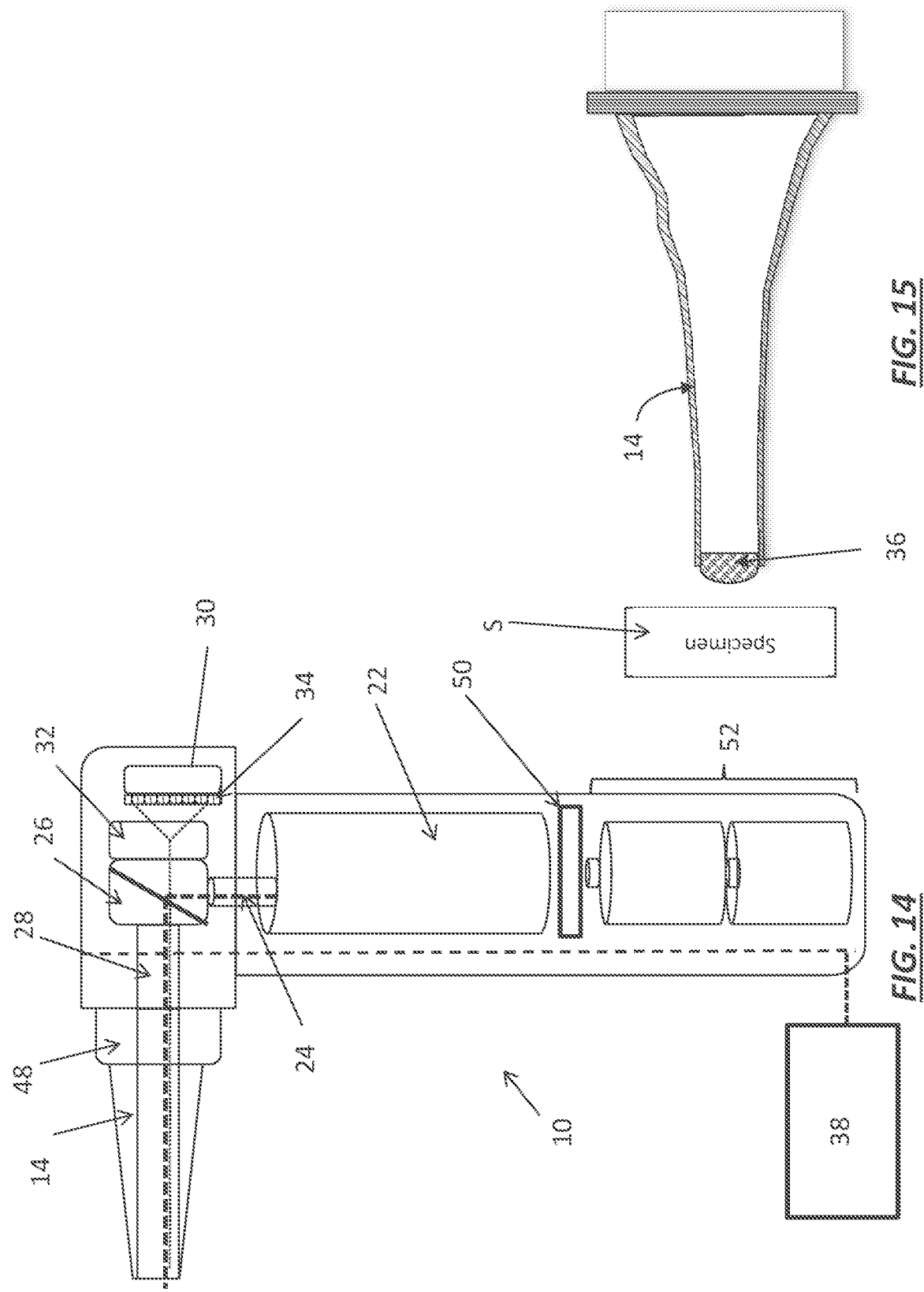

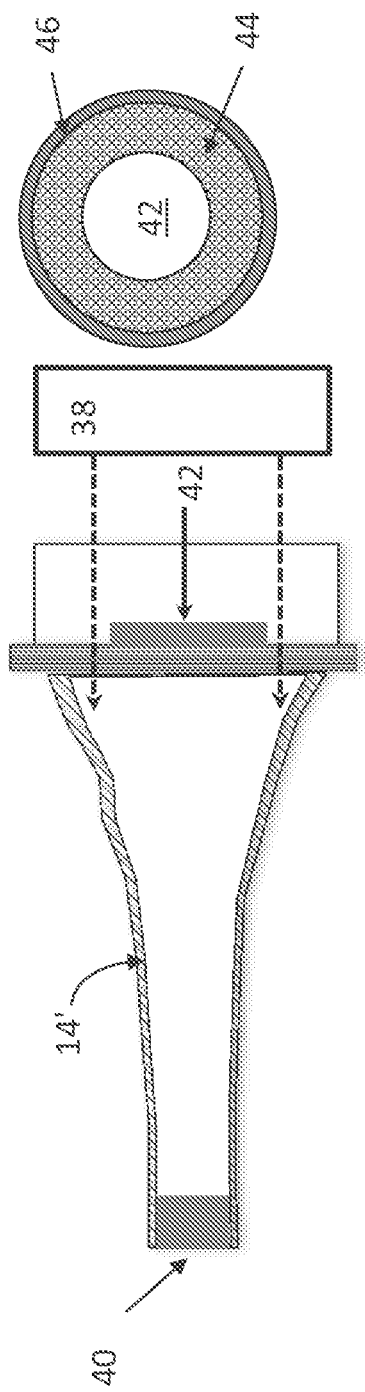
FIG. 16
FIG. 17
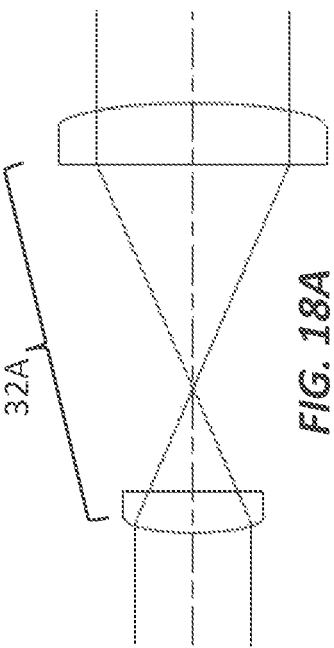
FIG. 18A
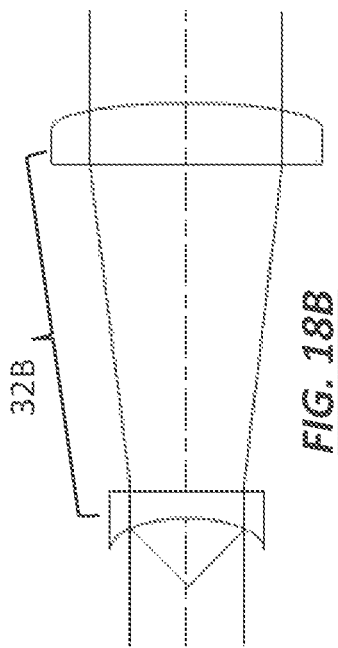
FIG. 18B

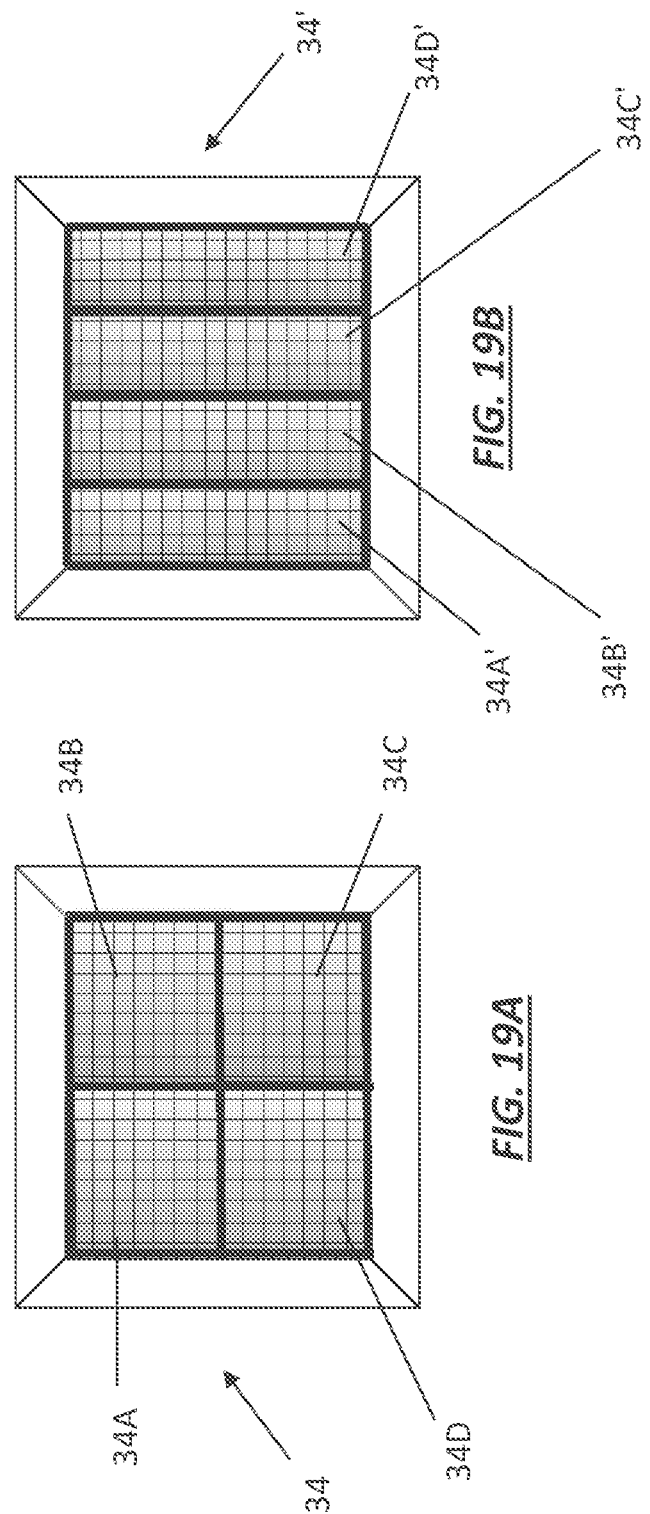

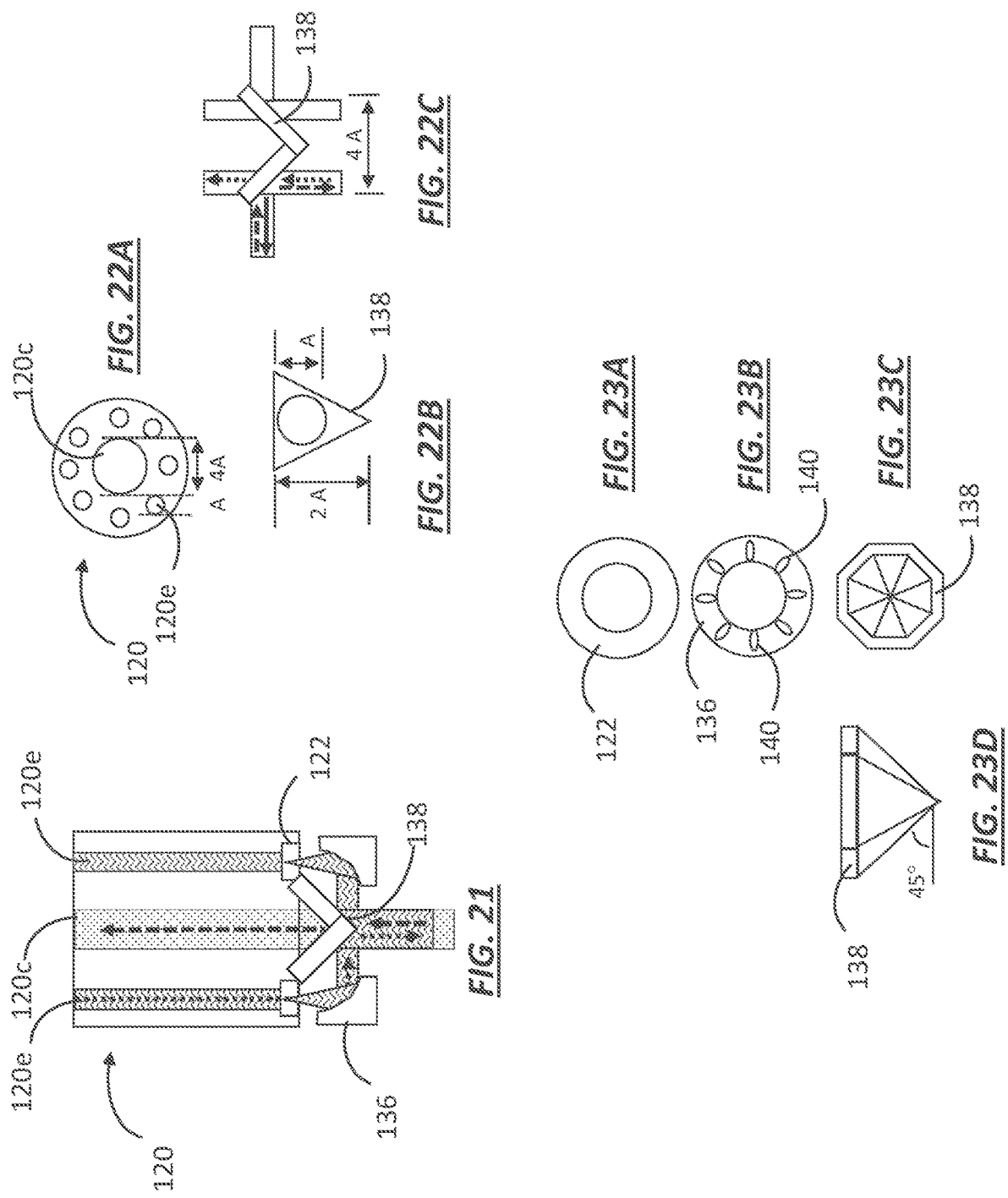

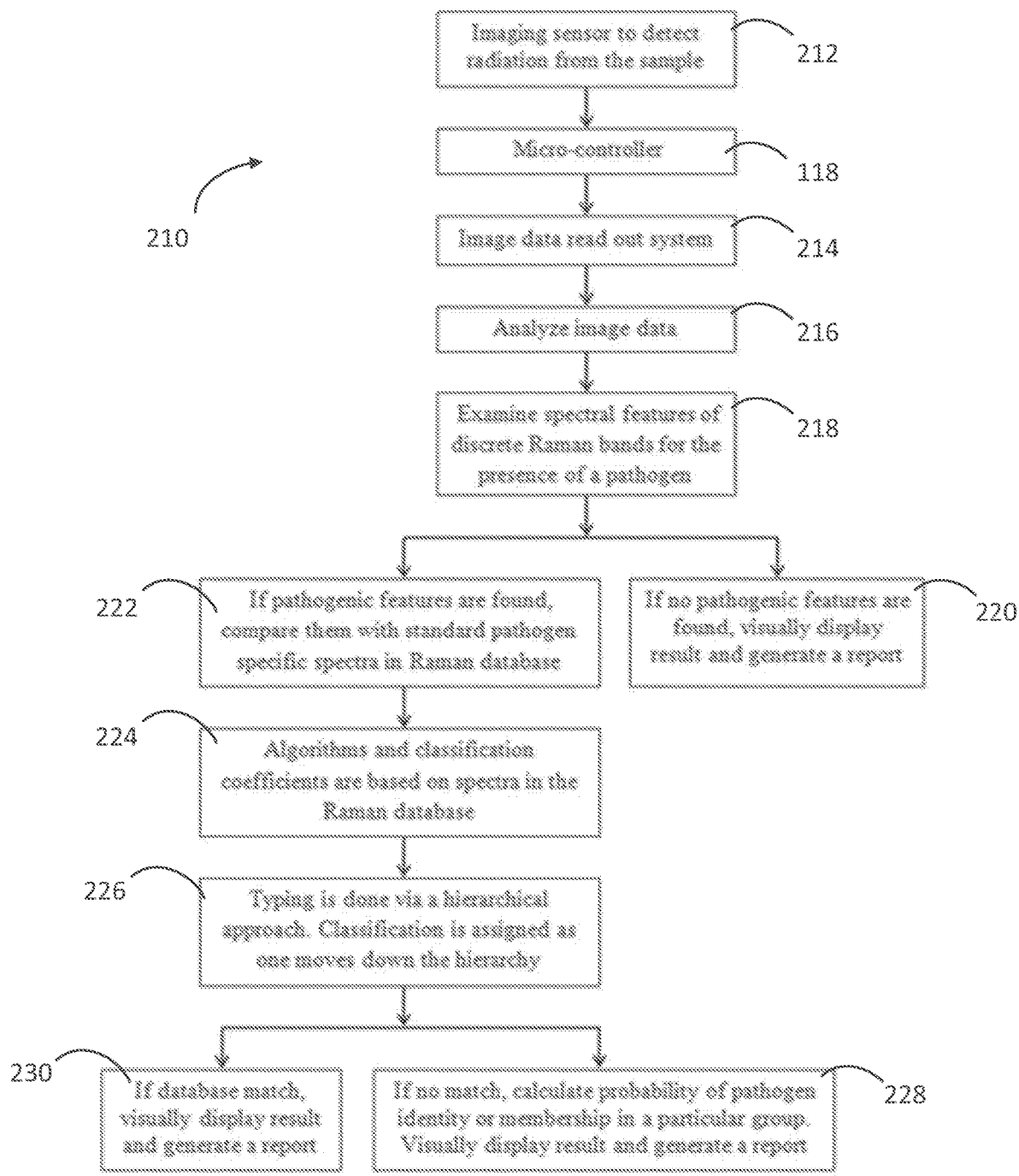
FIG. 25¶

RAMAN BASED DETECTION INSTRUMENT AND METHOD OF DETECTION

CROSS-REFERENCE TO RELATED APPLICATIONS

This is a continuation of U.S. application Ser. No. 14/910,459, filed Feb. 5, 2016, now U.S. Pat. No. 10,253,346, which is a national phase entry of International Application No. PCT/US2014/050182, which claims the benefit of U.S. Provisional Application No. 61/893,095, filed on Aug. 7, 2013, all of which are incorporated herein by reference.

FIELD

The present disclosure relates to a method and apparatus for rapidly detecting and identifying protein-based compounds including bacteria, virus, drugs, or tissue abnormalities, and more particularly a portable Raman spectroscopy based spectroscope which is adaptable for examining mucosal surfaces (nares, oral, ear), interrogating a wound site and/or inspection of a potentially contaminated object or surface for protein-based compounds including MRSA or other pathogens. The device can be adapted to interrogate tissue specimens, stool, urine, serum or secretions.

BACKGROUND

This section provides background information related to the present disclosure which is not necessarily prior art.

Methicillin resistance of *Staphylococcus aureus* (MRSA) is determined by the mecA gene which is carried by a mobile genetic element, designated staphylococcal cassette chromosome mec (SCCmec). MecA encodes a beta-lactam-resistant penicillin-binding protein called PBP2a (or PBP2'). Beta-lactam antibiotics normally bind to PBPs in the cell wall disrupting the synthesis of the peptidoglycan layer which results in bacterium death. However, since the beta-lactam antibiotics cannot bind to PBP2a, synthesis of the peptidoglycan layer and the cell wall continues. While the mechanism responsible for mecA transfer is still obscure, evidence supports horizontal transfer of the mecA gene between different staphylococcal species. Typically MRSA is diagnosed using culture based methods.

The Clinical and Laboratory Standards Institute (CLSI) recommends the cefoxitin disk diffusion test supplemented with the latex agglutination test for PBP2a. Phenotypic expression of resistance can vary depending on the growth conditions, as well as on the presence of subpopulations of staphylococci that may coexist (susceptible and resistant) within a culture making susceptibility testing by standard microbiological methods potentially problematic. In addition, culture takes time, usually 1 to 5 days. Faster techniques of MRSA screening by molecular methods, such as Polymerase Chain Reaction (PCR), have been developed to test for the mecA gene that confers resistance to methicillin, oxacillin, nafcillin, and dicloxacillin and other similar antibiotics. Such techniques, while faster, still take hours and are sent out to labs. In addition, commercially available molecular approaches (used for screening) are unable to detect mecA-variants of MRSA.

Raman spectroscopy is a reagentless, non-destructive, technique that can provide the unique spectral fingerprint of a chemical and/or molecule allowing for target identification without sample preparation. With this technique, a sample is irradiated with a specific wavelength of light whereby a small component, approximately 1 in $10^7$ photons, is in-elastically scattered (at wavelengths shifted from the incident radiation). The inelastic scattering of photons, due to molecular vibrations that change the molecule's polarizability, provide chemical and structural information uniquely characteristic of the targeted substance. Raman Spectroscopy can be extremely useful in fully characterizing a material's composition, and allows for relatively fast identification of unknown materials with the use of a Raman spectral database. In addition, since Raman Spectroscopy is a non-contact and non-destructive technique, it is well suited for in-situ, in-vitro and in-vivo analysis.

Raman Spectroscopy has high potential for screening of bacteria, virus, drugs, as well as tissue abnormalities since it: 1) is practical for a large number of molecular species; 2) can provide rapid identification; and 3) can be used for both qualitative and quantitative analysis. A portable or handheld micro Raman based detection instruments would be useful to reliably and rapidly assess *Staphylococcus aureus* strains in wounds or nasal passages. Rapid assessment and typing would enable tracking the spread of such pathogens and could significantly decrease the number of hospital-acquired infections and the associated costs in treatment thereof.

SUMMARY

This section provides a general summary of the disclosure, and is not a comprehensive disclosure of its full scope or all of its features.

A hand-held Raman spectroscopy based device system for mucosal examination (nares, oral, ear) and wound interrogation provides a method for rapid and cost effective screening of bacteria, virus, drugs, and tissue abnormalities. The device is a nonintrusive automated near-real-time-point-of-care detection system that can enable healthcare providers to render better patient management and optimize clinical outcomes. The device includes a disposable tip element having dimensions that are small enough to fit into a small body cavity, such as the nostril. Three types of tip elements may be employed with this system—one for direct nasal interrogation, one with vacuum suction and filter, and one with proximity optics for wound interrogation. The tip element and the device enclose an assembly of optical components which allow for Raman spectral measurement that can provide the unique spectral fingerprint of a chemical and/or molecule allowing for target identification without sample preparation.

The device incorporates signal processing and identification algorithms for signal conditioning and target detection. Combinations of ultra-high resolution micro-filters in discrete regions (e.g., quadrants) of an area on the imaging detector array provide specific analysis of target spectral peaks. Each region or quadrant allows for discrete spectral band detection with each micro-filter providing specific wavenumber detection for spectral analysis. Discrete Raman spectral bands that distinguish a targeted substance from background interference are used to develop learning algorithms that serve as a basis for detection and target identification. By obtaining data at discrete spectral regions instead of over the entire spectral rage, acquisition time as well as spectral contributions from confounding background interference will be reduced or eliminated allowing for near-real-time assessment.

Methods for identification of pathogens in fluidic samples using Raman spectroscopy also form a part of the present disclosure. These methods show use a limited number of discrete spectra peaks to sample key molecular identifiers of a wide range of potential targets for specific pathogen detection. As a result, the apparatus and methods described herein can be customized for a host of target materials and implemented in a relatively small, portable form factor. In essence, an adapted system is provided, which can be readily modified to change target needs by means of a built-in learning algorithm. An exemplary learning algorithm was developed under a United States Department of Defense program for real-time pathogen detection in water as well as for real-time identification of cancer cells from tissue samples and may be adapted into a detection protocol. After pre-processing is complete, a Discriminant Function Analysis (DFA) is used to classify samples. DFA predicts membership in a group. The independent variables are the predictors and the dependent variables are the groups, based on an assumption of multivariate normality. This resulting data is used to modify the Raman-based spectral analysis executed in the hand held device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 14 illustrates the components of the device shown in FIG. 12;

Figure 20:
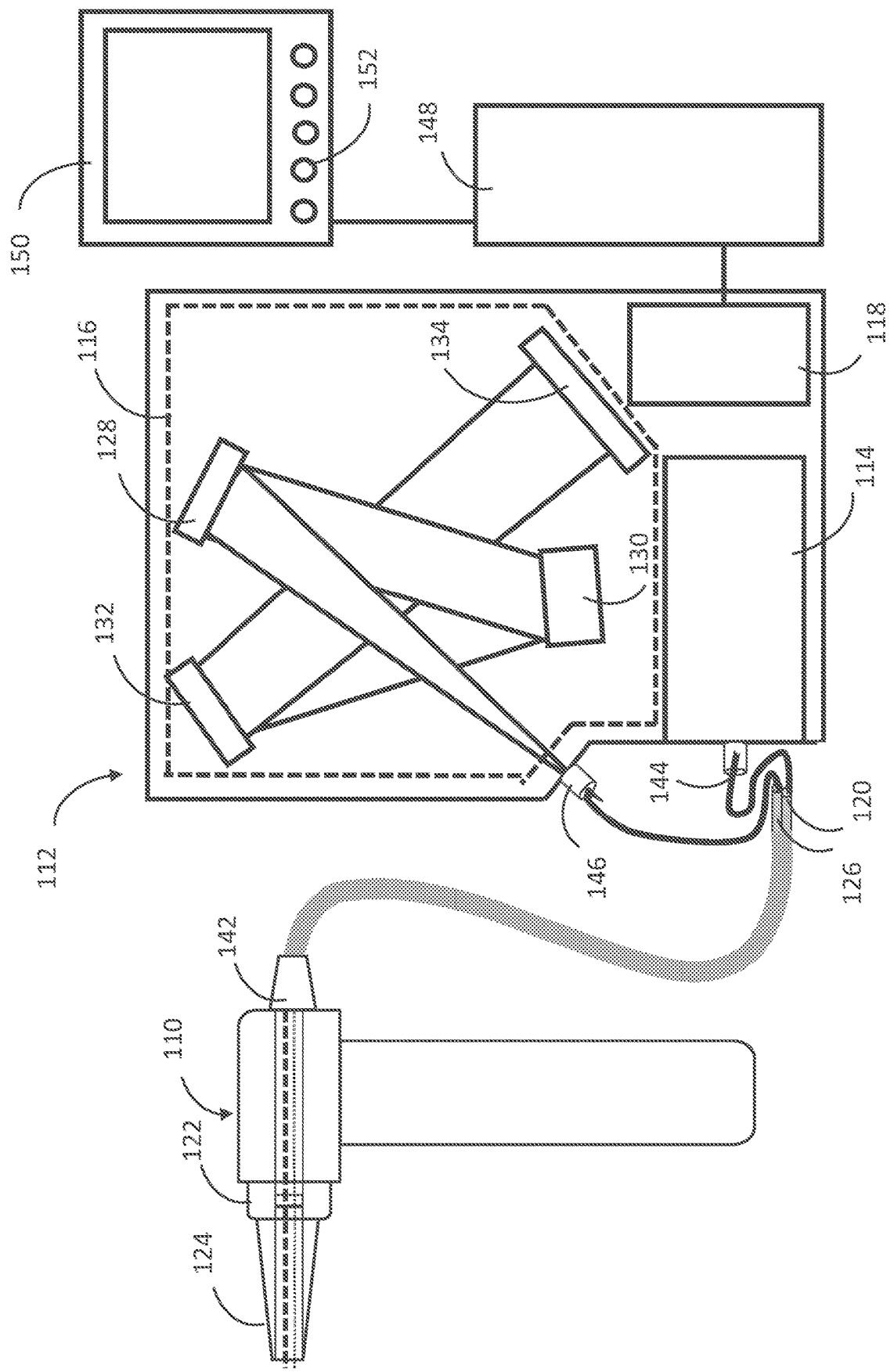
Figure 24:
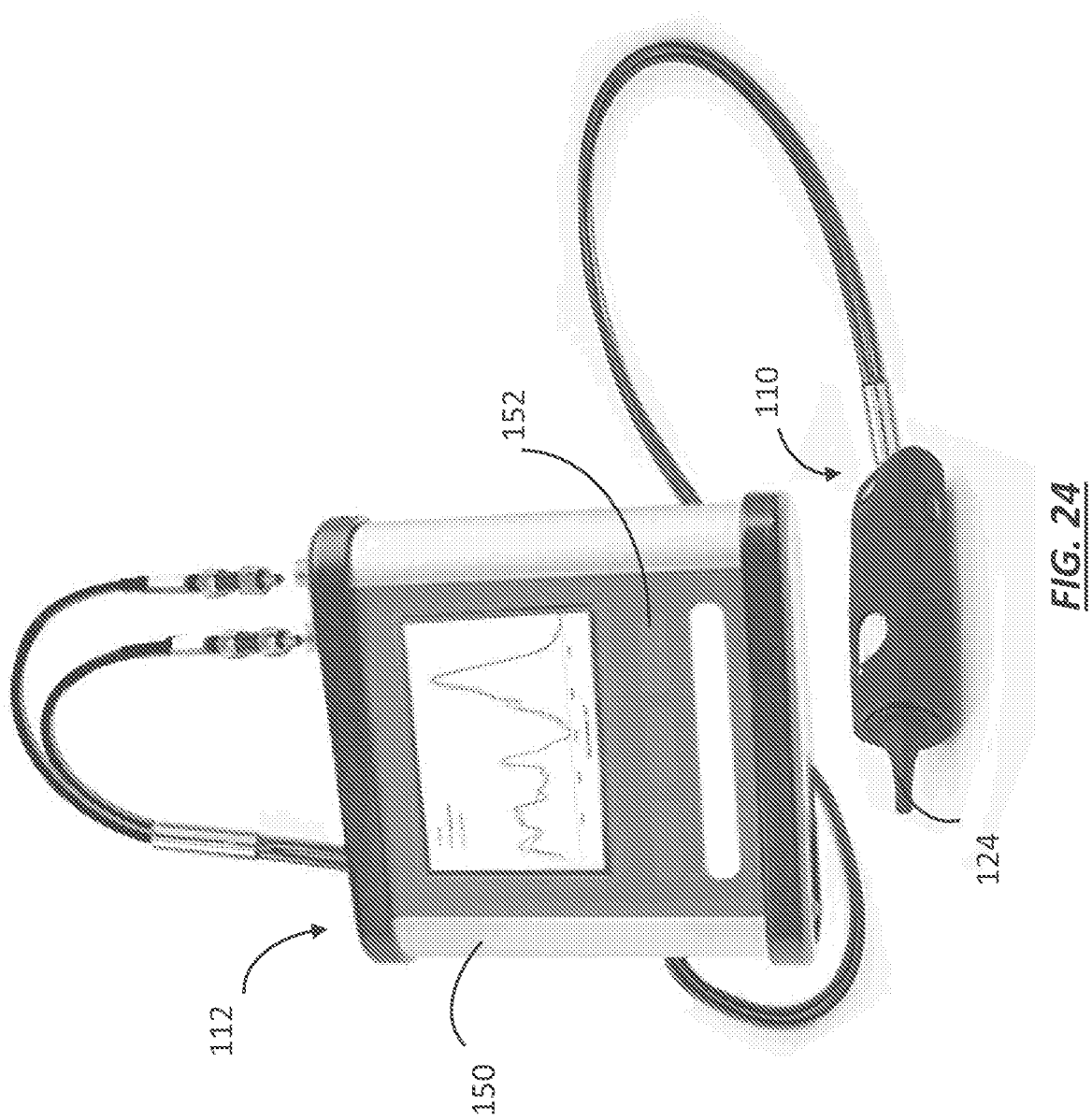

FIG. 15 a disposable end effector of the device for wound and/or nasal interrogation;

FIG. 16 illustrates a disposable end effector of the device with filtering function for vacuum suction application;

FIG. 17 is an end view of the end effector shown in FIG. 16;

FIGS. 18A and 18B illustrate simple examples of the beam expander shown in FIG. 14;

FIG. 19 illustrates the filter element shown in FIG. 14;

FIG. 20 illustrates another embodiment of a Raman probe and detection system;

FIG. 21 illustrates the optical components of the Raman probe shown in FIG. 20;

FIG. 22A-C illustrates detailed aspects of the optical components shown in FIG. 20;

FIG. 23A-D illustrates a laser line filter, off-axis parabolic mirror system and hexagonal conical lens for the Raman probe shown in FIG. 22;

FIG. 24 illustrates a portable form factor of the device shown in FIG. 20; and

FIG. 25 is a flow chart illustrating the operating procedures carried out during a pathogen detection procedure using the hand held micro-Raman based detection instrument.

Corresponding reference numerals indicate corresponding parts throughout the several views of the drawings.

DETAILED DESCRIPTION

Through preliminary studies explained in further detail below, the feasibility of Raman Spectroscopy to assess various protein-based compounds including numerous pathogens using a laboratory Raman Spectrometer is demonstrated. For these studies the following pathogens were evaluated in the absence of background interference:

MSSA-1S: *Staphylococcus aureus* subsp. *aureus* (ATCC® 6538 ™);
MSSA-2S: *Staphylococcus aureus* subsp. *aureus* (ATCC® BAA1721 ™);
MRSA-1R: *Staphylococcus aureus* (ATCC® BAA1683™);
MRSA-2R: *Staphylococcus aureus* subsp. *aureus* (ATCC® 700787 ™);
*Corynebacterium* sp. (ATCC® 6931 ™);
*Staphylococcus epidermidis* (ATCC® 12228™);
Influenza APR8/34 (H1N1);
Influenza A/WSN/32 (H1N1); and
Influenza A/Udorn/72 (H2N3).

Preliminary studies on additional pathogens (such as *Bacillus subtilis, E. coli* K99, *E. coli* O111, *E. coli* O157, *Enterobacter amnigenus, Listeria monocytogenes, Pseudomonas aeruginosa, Rahnella aquatilis, Salmonella Schottmueller, Salmonella Typhimurium, Streptococcus pneumonia, Vibrio fluvialis*, and *Staphylococcus epidermidus*—ATCC #35984) demonstrate the feasibility of identification by Raman Spectroscopy as further described herein. These results provide a positive indication that a Raman spectral database for a wide variety of protein-based compounds could be developed with analysis protocols that allow for target identification and classification. As such the system and method described herein is not limited to examination, detection and identification of MRSA and/or influenza but has a broader range of application to examination, detection and identification of various pathogens, toxins and other protein-based compounds.

The MRSA-2R strain of *Staphylococcus aureus* has reduced susceptibility to vancomycin and was isolated from human blood from a patient with fatal bacteremia. The MSSA-2S strain of *Staphylococcus aureus* is a hyper-virulent community acquired methicillin-susceptible strain isolated in the United Kingdom. It is a complete genome sequenced strain. The MRSA 1R strain of *Staphylococcus aureus* is Methicillin resistant and was isolated from a human abscess. It is confirmed to carry the mec A gene with a SCCmec, or staphylococcal cassette chromosome mec type IV and PFGE type USA 400. The MSSA-1S strain of *Staphylococcus aureus* is Methicillin sensitive and was isolated from a human lesion [ATCC].

*Staphylococcus epidermidis* and *Corynebacterium* are normal flora found in the nose. *Staphylococcus epidermidis* with Corynebacteria predominantly colonizes the upper respiratory tract, especially the nostrils. *S. epidermidis* accounts for 90%-100% of the staphylococci found in the nasal cavity when *S. aureus* is not present. However, when *S. aureus* is present, the amount of *S. epidermidis* drastically decreases. Most species of *Corynebacterium* will not cause diseases in humans, however; *Corynebacterium diptheriae* NCTC 13129 is a strain that is highly infectious.

Samples were prepared from bacteria plated on tryptic soy agar plates. A single colony was picked and added to 5 mls of tryptic soy broth in a 10 ml culture tube. The culture tube was place on a shaker in a 37 C incubator and incubated overnight. The next day an optical density (OD) was taken to verify the consistency of the growth conditions and to provide a reference OD. The overnight culture was centrifuged at room temperature for 5 min @ 3000 rpms. After centrifuging the supernatant was removed and the bacteria pellet was resuspended with 5 mls of filtered tap water. The bacteria were centrifuged as stated and the washing process was repeated 2 more times. On the final wash the OD of the solution was measured and if the OD was greater than 1.05, water was added until an OD of 1+0.05 was obtained. 150 ul of the bacteria suspension was then placed on a UV quartz substrate (Craic technologies) for Raman spectroscopy.

Raman spectra were recorded with an in-via Raman microscope (Renishaw®) equipped with a 1800 l/mm grating, a 50 mW 514.5 nm laser as the excitation source at 100% laser power. The laser light was focused onto the sample though a 63× dipping objective (Leica HCX PL APO 1.2NA Corr/0.17 CS). The spectra were acquired over a spectral range of 400-3200 cm-1 with 40 accumulations at an integration time of 10 s.

Figure 1:
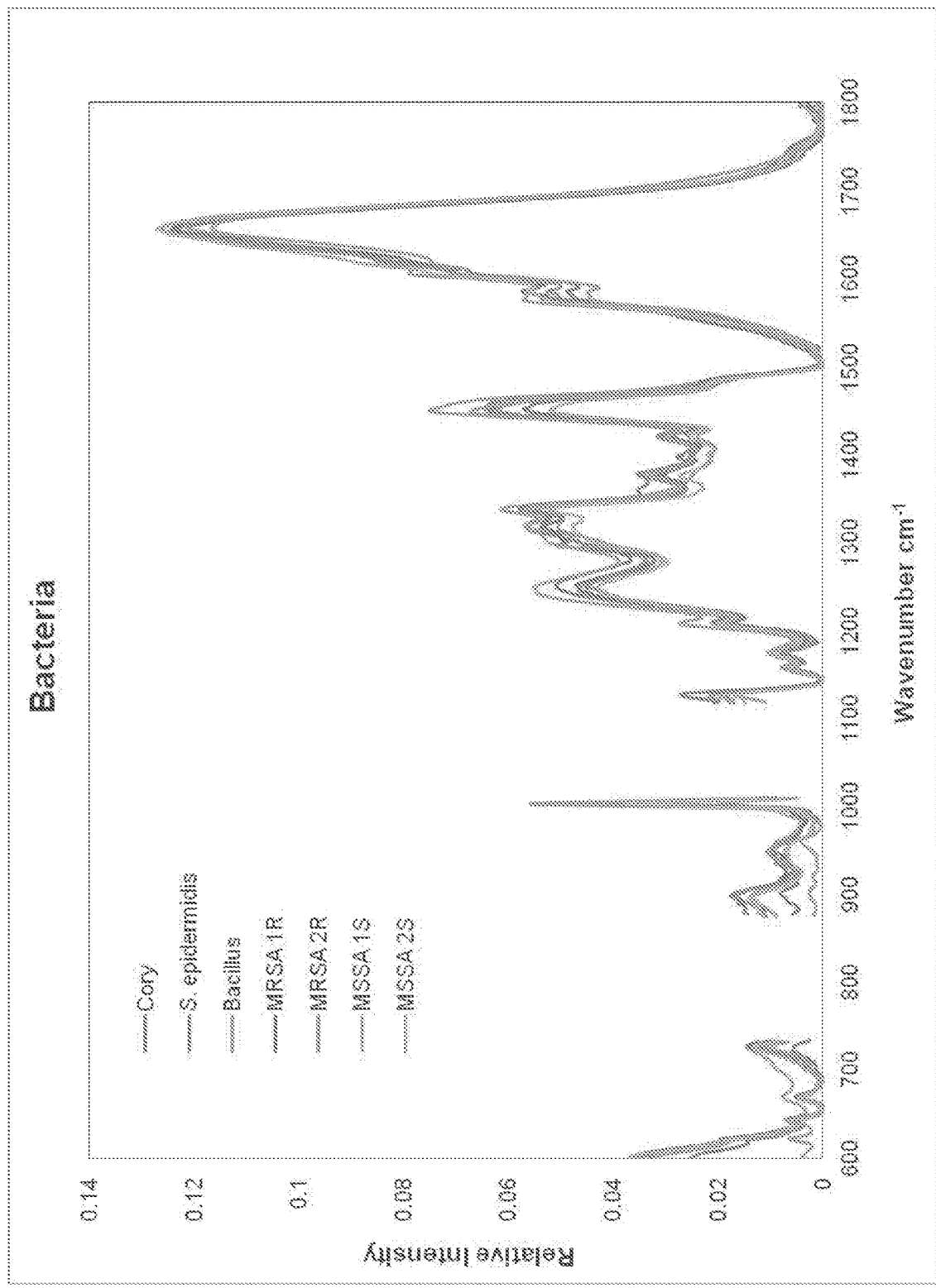
FIG. 1 illustrates the mean spectra for various bacteria in terms of the relative intensity as a function of wavelength.
Figure 2:
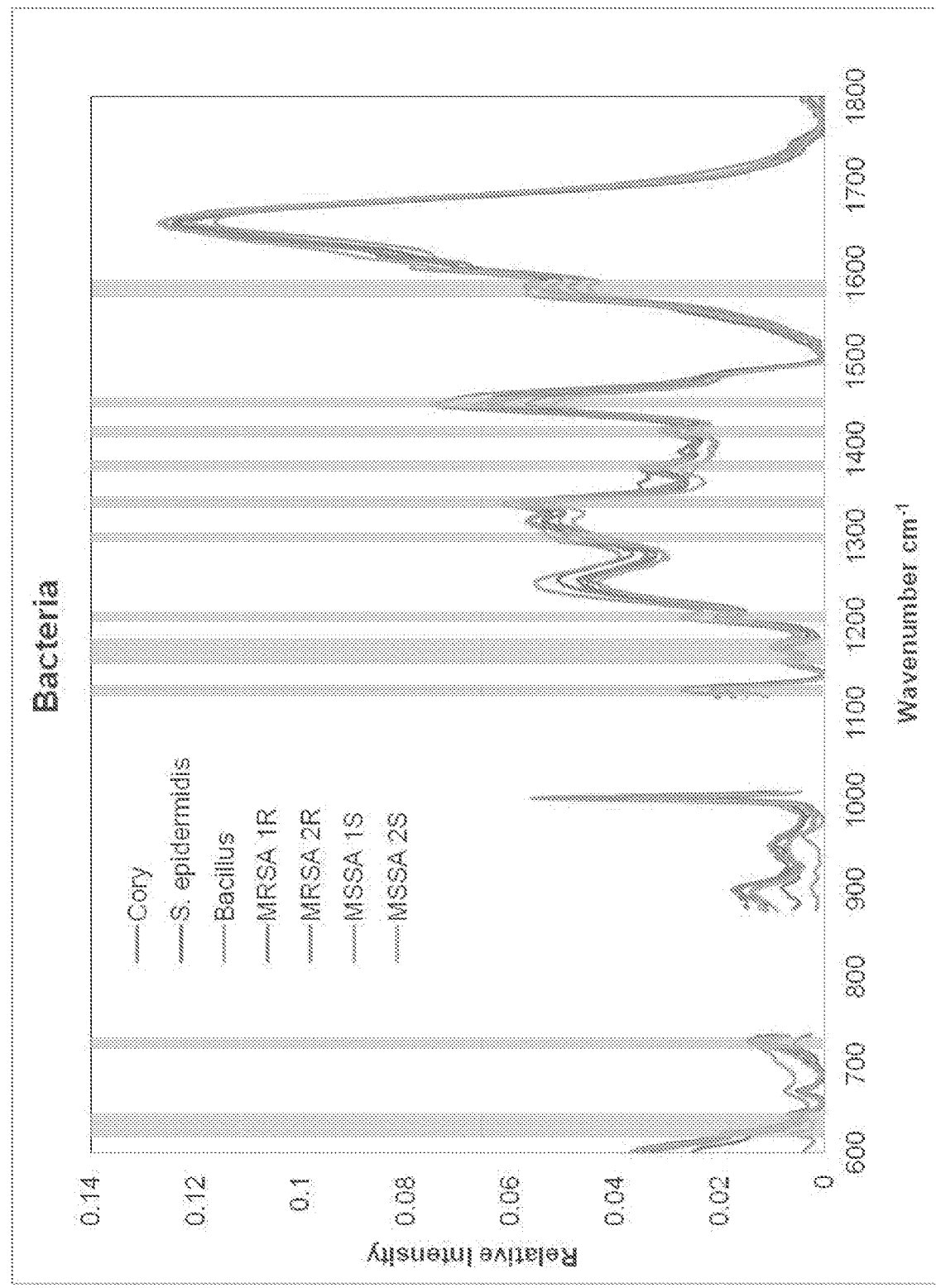
FIG. 2 illustrates the wave numbers or spectral bands ascertained with DFA distinguishing the tested bacteria.
Figure 3:
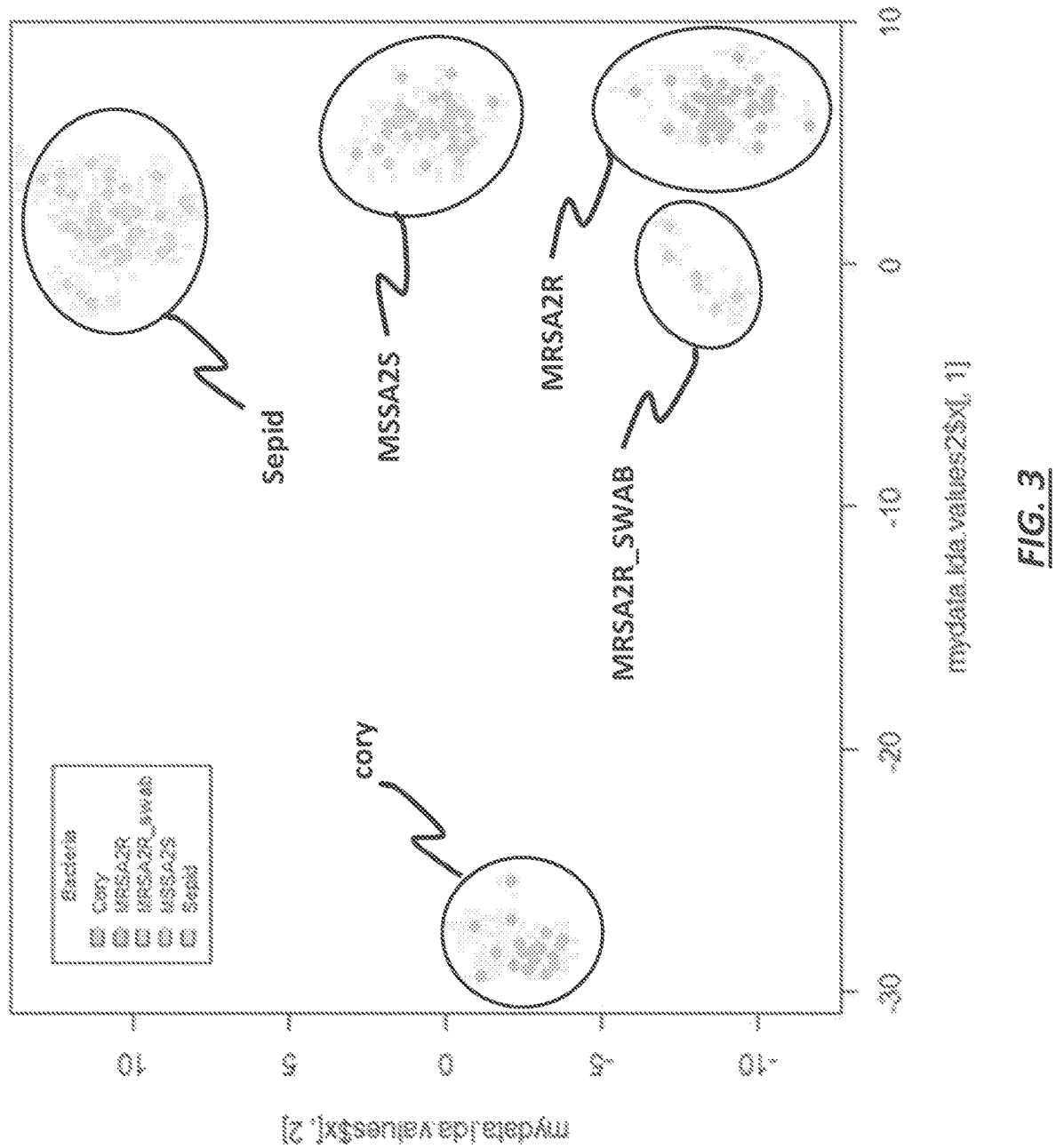
FIG. 3 illustrates a cluster analysis of Raman spectra of bacteria.

Prior to analysis, spectra were pre-processed using: (1) derivative smoothing with a sliding window of 5; (2) range exclusion in the region of 735-874 cm-1 and 1013-1116 cm-1 to eliminate quartz dominated spectral regions; (3) background subtraction via a robust polynomial fit to remove spectral contributions due to fluorescence; and (4) vector normalization to reduce bacteria concentration effects. The mean Raman spectra are shown in FIG. 1.

A key to developing the Raman spectroscopy based detection device is the development of a Raman spectral database with analysis protocols that allow for target identification and classification. As part of the analysis protocol, Raman spectral bands that can distinguish a targeted substance from background interference are identified. These discrete bands are used to develop learning algorithms that serve as a basis for detection and identification. By obtaining data at discrete spectral regions instead of over the entire spectral range (600-1800 cm-1), acquisition time as well as spectral contributions of confounding background interference can be reduced. The spectroscopic system with discrete spectral band identification for algorithms development is detailed in embodiments of the device.

To identify discrete spectral bands of statistical significance, the pure spectra of bacteria in water were analyzed using discriminant function analysis, DFA (IBM SPSS Statistics 21). DFA builds a predictive model for group membership. The model is composed of discriminant functions that are based on linear combinations of predictor variables. Spectral data, that is to say wavenumber with associated Raman intensity, corresponding to the following Raman peaks were utilized: 600, 621, 643, 670, 725, 896, 935, 960, 1003, 1126, 1158, 1173, 1209, 1249, 1297, 1320, 1338, 1362, 1375, 1397, 1420, 1449, 1480, 1578, 1584, 1606, 1620, 1640, 1657 cm-1. Stepwise discriminant function analysis is used to reduce the number of variables (wavenumbers) to a subset of input into simultaneous discriminant analysis for classification. Once the model is finalized, cross validation is done based on the "leave one-out" principle in which one individual is removed from the original matrix and the discriminant analysis is then performed from the remaining observations and used to classify the omitted individual.

A similar procedure and analysis can be used for other pathogens such as the influenza virus described herein, as well as numerous other protein-based compounds.

The analysis for identifying the MRSA strains of bacteria is done based upon 2-group classification scheme. First an investigation of the ability of Raman spectroscopy to distinguish the *Staphylococcus* genus from other genus of bacteria is conducted. The *Staphylococcus* group consisted of MRSA 1R, MRSA 2R, MSSA 1S, MSSA 2S, and *S. epidermidis*, while the non-*Staphylococcus* group consisted of *Bacillus subtilis*, and *Corynebacterium* sp. The classification results show that 100% of cross-validated grouped cases correctly classified with 100% of the *Staphylococcus* group and 100% of the non-*Staphylococcus* group correctly classifying. Five wavenumbers were utilized in the discriminant model; 725 cm-1, 1158 cm-1, 1209 cm-1, 1420 cm-1, and 1450 cm-1, corresponding to vibrations of nucleic acids, proteins and lipids. Raman vibrational band assignments are given in Table 1 shown below.

TABLE 1

| Wavenumber cm$^{-1}$ | Tentative Assignments from Literature | Location |
|---|---|---|
| 620, 640 | Amino acids (620 cm$^{-1}$ = phenylalanine, 640 cm$^{-1}$ = tyrosine) | Protein |
| 665-782 | Nucleic acids (G,A,C,T,U) | DNA/RNA |
| 788 | O—P—O sym str. | DNA |
| 810-820 | Nucleic acids (C—O—P—O—C), A-type helix | RNA |
| 829, 852 | Tyrosine (buried, exposed) | Protein |
| 877-937 | Protein [v(C—C)], carbohydrates [v(COC)], lipids | Carbohydrates, protein, lipids |
| 1003 | Phenylalanine v(C—C) ring breathing | Protein |
| 1030-1085 | Protein[ v(C—N), v(C—C)], carbohydrate [v(C—O), v(C—C)], lipids | Protein, carbohydrate, lipids |
| 1095 | DNA: PO$_2$- str (sym) | DNA |
| 1126 | Protein [(v(C—N), v(C—C)], lipids[v(C—C)], carbohydrates [v(C—C), v(COC) glycoside link] | Protein, lipids, carbohydrates |

TABLE 1-continued

| Wavenumber cm$^{-1}$ | Tentative Assignments from Literature | Location |
|---|---|---|
| 1158 | Protein [v(C—C)] | Protein |
| 1175 | Aromatic amino acids, Tyrosine [δ(C—H)], | Protein |
| 1230-1295 | Amide III [v(C—N), N—H bend, C=O, O=C—N bend], 1230 cm$^{-1}$ = sat lipid | Protein, nucleic acids, lipids |
| 1295, 1267 | Lipids [δ(CH$_2$)] likely unsaturated | Lipids |
| 1320-1340 | Nucleic acids (Guanine, Adenine), proteins, carbs (1340 cm$^{-1}$) | DNA/RNA, proteins, carbohydrates |
| 1336 | Amino acids [C—H bend] | Protein |
| 1375 | Nucleic acids (T,A,G) | DNA |
| 1420-1460 | Lipids, carbohydrates, proteins [δ(C—H$_2$) scissoring for each] | Lipids, carbohydrates, proteins |
| 1483-1487 | Nucleic acid (G, A), CH def. | DNA |
| 1518-1550 | Amide II [N—H bend, v(C—N), v(C=C)] | Protein |
| 1575-1578 | Nucleic acids (G, A), ring stretching | DNA |
| 1585 | Tryptophan, Phenylalanine | Protein |
| 1606 | Phenylalanine, Tyr. | Protein |
| 1617 | Tyrosine, Trp. | Protein |
| 1640 | Water | |
| 1650-1680 | Amide I [v(C=O), v(C—N). N—H bend], Lipid [C=C str] | Protein, Lipid |
| 1735 | >C=O ester str. | Lipids |

Next, the feasibility of Raman spectroscopy to distinguish MRSA from other *Staphylococcus* species and strains is determined. The analysis continues all the way to stain identification. The DFA classification results are provided in Table 2 shown below.

TABLE 2

| Groups | Cross-validated Results | Wavenumbers for the DF |
|---|---|---|
| Genus | | |
| Group 1: *Staphylococcus* Group 2: *Bacillus* and Cory | 100% of cross-validated grouped cases correctly classified with 100% *Staphlocollus* and 100% (Cory and *Bacillus*) correctly classifying. | 5 wavenumbers Nucleic acids (725 cm$^{-1}$), Protein (1158 ccm$^{-1}$, 1209 cm$^{-1}$), Lipids/protein (1420 cm$^{-1}$), Lipids/protein/carbohydrates (1450 cm$^{-1}$) |
| MRSA from other staph | | |
| Group 1: MRSA1R and MRSA 2R Group 2: MSSA 1S, MSSA 2S, and *S. epidermidis* | 90.7% of cross-validated grouped cases correctly classified with 89.9% MRSA and 91.3% (MSSA and *S. epidermidis*) correctly classifying. | 6 wavenumbers Protein (621 cm$^{-1}$, 1173 cm$^{-1}$, 1338 cm$^{-1}$). Protein, lipids, carbohydrates (1126 cm$^{-1}$), Lipid (1297 cm$^{-1}$), Lipids/protein (1420 cm$^{-1}$) |
| MRSA 1R vs MRSA 2R | | |
| Group 1: MRSA 1R Group 2: MRSA 2R | 100% of cross-validated grouped cases correctly classified with 100% MRSA 1R and 100% MRSA 2R correctly classifying. | 3 wavenumbers Nucleic acids (1320 cm$^{-1}$, 1584 cm$^{-1}$), Lipids/protein/carbohydrates (1375 cm$^{-1}$) |
| MSSA from *S. epidermis* | | |
| Group 1: MSSA 1S and MSSA 2S Group 2: *S. epidermidis* | 93.8% of cross-validated grouped cases correctly classified with 93.9% *Staphlocollus* and 93.5% (Cory and *Bacillus*) correctly classifying. | 5 wavenumbers Protein (642 cm$^{-1}$, 1338, cm$^{-1}$). Protein, lipids, carbohydrates (1126 cm$^{-1}$, 1450 cm$^{-1}$), Nucleic acids (1578 cm$^{-1}$) |
| MSSA 1S from MSSA 2S | | |
| Group 1: MSSA 1S Group 2: MSSA 2S | 100% of cross-validated grouped cases correctly classified with 100% MSSA1S and 100% MSSA 2S correctly classifying. | 2 wavenumbers Lipid/protein (1420 cm$^{-1}$), Lipids/protein/carbohydrates (1450 cm$^{-1}$) |

The first column in Table 2 lists members of each group. The second column lists the cross-validated classification results. The third column lists the specific wavenumbers utilized in the Discriminant function models which are shown accumulatively in FIG. 4. The results of this analysis indicate that MRSA can be separated from other bacteria down to the strain level using a minimal number of Raman spectral bands. Further, methacillin sensitive strains of bacteria can also be distinguished and identified.

Next, the detection of a target pathogen with a confounding background is considered. For nasal analysis, background interference from potential confounding factors is assessed. *S. aureus* most commonly colonizes the anterior nares (the nostrils), although the respiratory tract, opened wounds, intravenous catheters, and urinary tract are also potential sites for infection. Since there are other bacteria and material in the exterior nares, it is important to investigate the ability to separate MRSA from other species of bacterium and confounding factors. Prominent nasal flora include *Staphylococcus aureus, Staphylococcus epidermidis* cells, *Corynebacterium* sp., and *Propionibacterium* sp. Nasal secretions may also include Mucin, Epithelial Cells and red blood cells.

Figure 5:
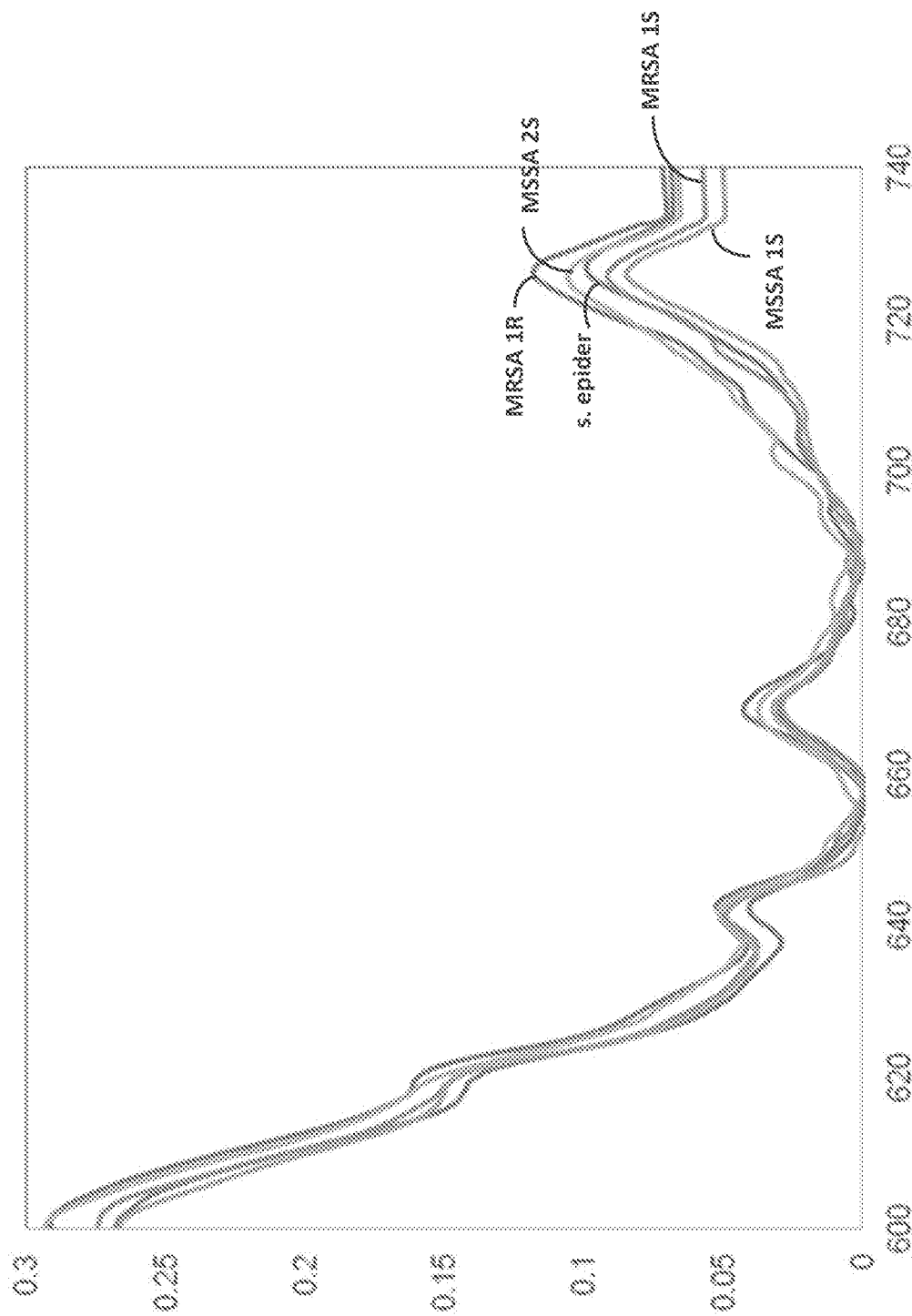
FIG. 5 illustrates the mean spectra of *Staphylococcus* with an expanded view of minimally obstructed spectral regions 600-740 (cm-1)

For this work nasal swab samples are taken and inoculated with MRSA 1R, MRSA 2R, MSSA 1S or *S. epidermidis*. To determine if MRSA can be distinguished in the presence of nasal secretions, a cluster analysis is performed. The pure spectra, of *Corynebacterium* sp., *Staphylococcus epidermidis*, MSSA 2S and MRSA 2R in water as well as the spectra of nasal swab samples inoculated with MRSA 2R are analyzed. FIG. 5 show the results of a cluster analysis. The results show that nasal swab samples inoculated with MRSA 2R are grouping with pure samples of MRSA 2R indicating that Raman spectroscopy can be used to distinguish bacteria in the presence of confounding factors.

Figure 6:
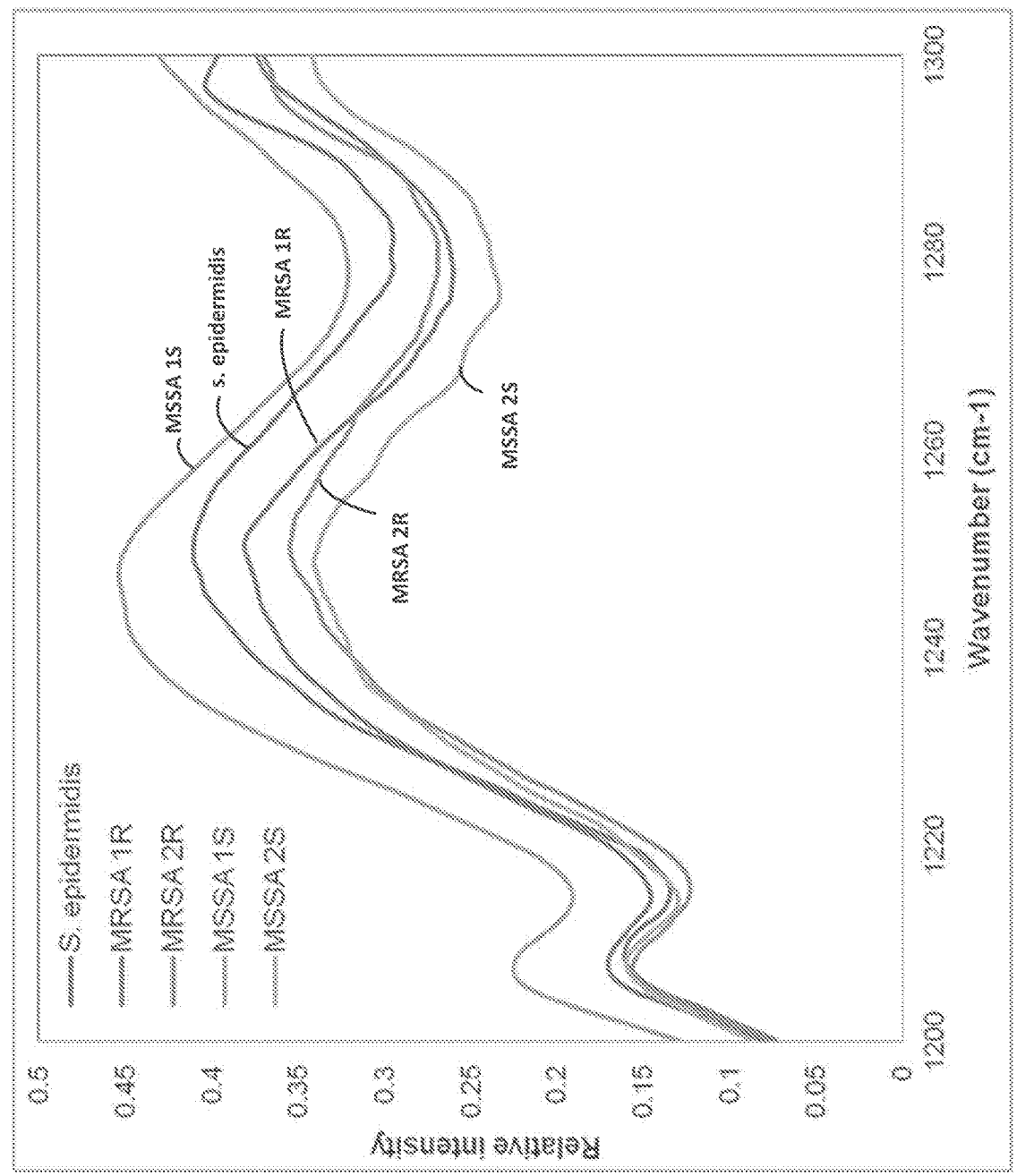
FIG. 6 illustrates the mean spectra of *Staphylococcus* with an expanded view of minimally obstructed spectral regions 1200-1300 (cm-1)

To determine regions of the Raman spectra that are not dominated by background interference, the pure spectra of MRSA 1R (in the absence of background factors) was overlaid on the spectra of inoculated nasal swab samples. FIG. 6 indicate that regions around 640-740, 1200-1265, 1520-1560 and 1620-1700 cm-1 have minimal background contribution.

The spectra shown in FIG. 6 are pre-processed slightly different than those shown in previous figures. Due to the large intense peaks of background components, spectra were pre-processed with (1) derivative smoothing using a sliding window of 5; (2) background subtraction via a robust polynomial fit to remove spectral contributions due to fluorescence; and (3) normalization using the 1657 cm-1 peak as opposed to vector normalization.

The pure spectra, of bacteria in water, were re-analyzed with DFA using data only in the regions 640-740, 1200-1265 cm$^{-1}$. The ability of Raman spectroscopy to distinguish the *Staphylococcus* genus from other bacteria genus is shown in below. Five wavenumbers are utilized in the discriminant model; 640 cm$^{-1}$, 672 cm$^{-1}$, 725 cm$^{-1}$, 1209 cm$^{-1}$, and 1225 cm$^{-1}$, corresponding to vibrations of nucleic acids, and proteins.

TABLE 3

| Groups | Cross-validated Results | Wavenumbers for the DF |
|---|---|---|
| Genus | | |
| Group 1: *Staphylococcus* Group 2: *Bacillus* and Cory | 94.5% of cross-validated grouped cases correctly classified with 95.8% *Staphylococcus* and 91.3% (Cory and *Bacillus*) correctly classifying. | 5 wavenumbers Protein (640 cm$^{-1}$, 1209 cm$^{-1}$), Nucleic acids (672 cm$^{-1}$, 725 ccm$^{-1}$), edge of Amide III peak (1225 cm$^{-1}$) |

Figure 8:
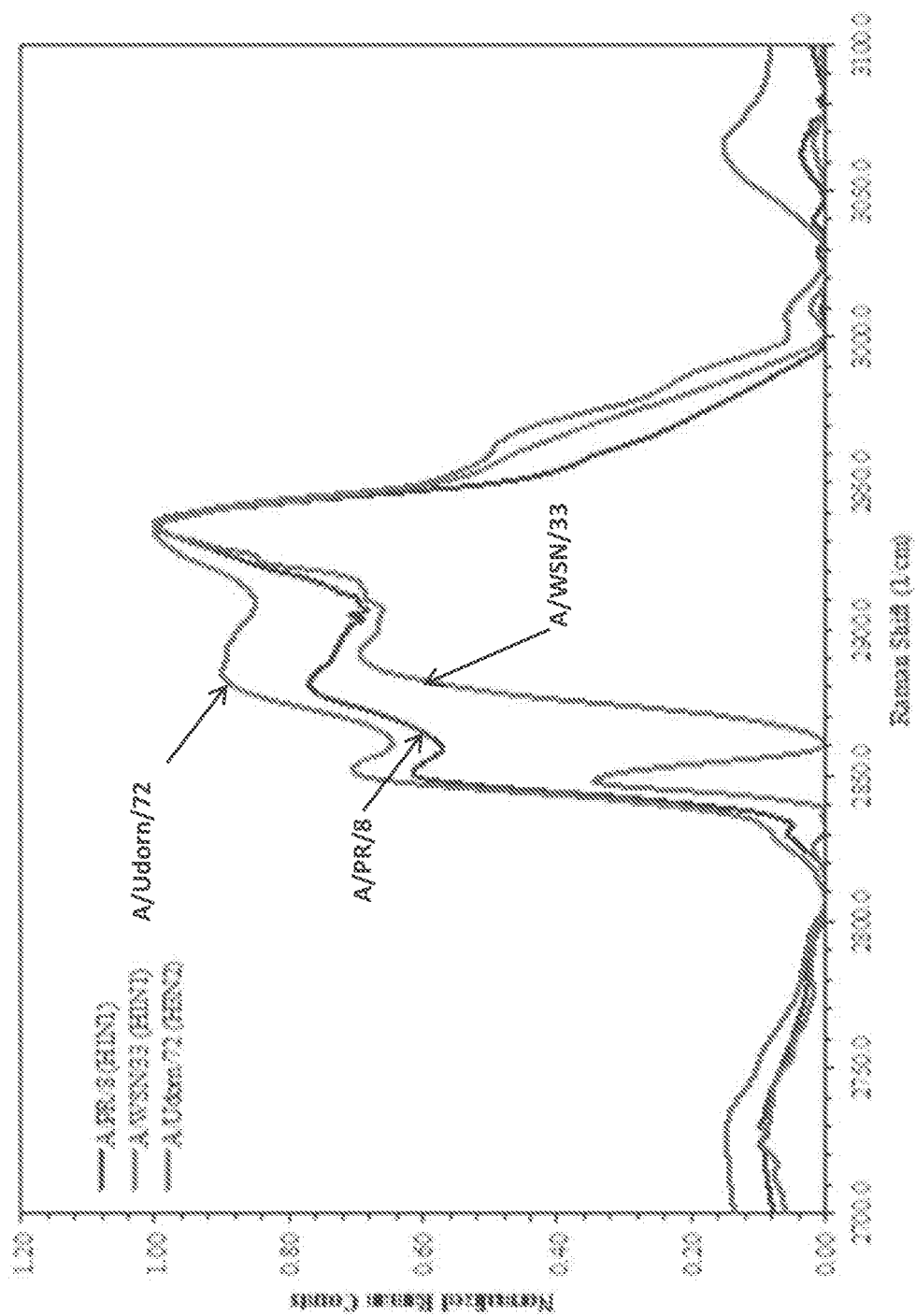
FIG. 8 illustrates spectral peaks for the three influenza virus at Raman shifts between 2850 and 2950 $cm^{-1}$.
Figure 9:
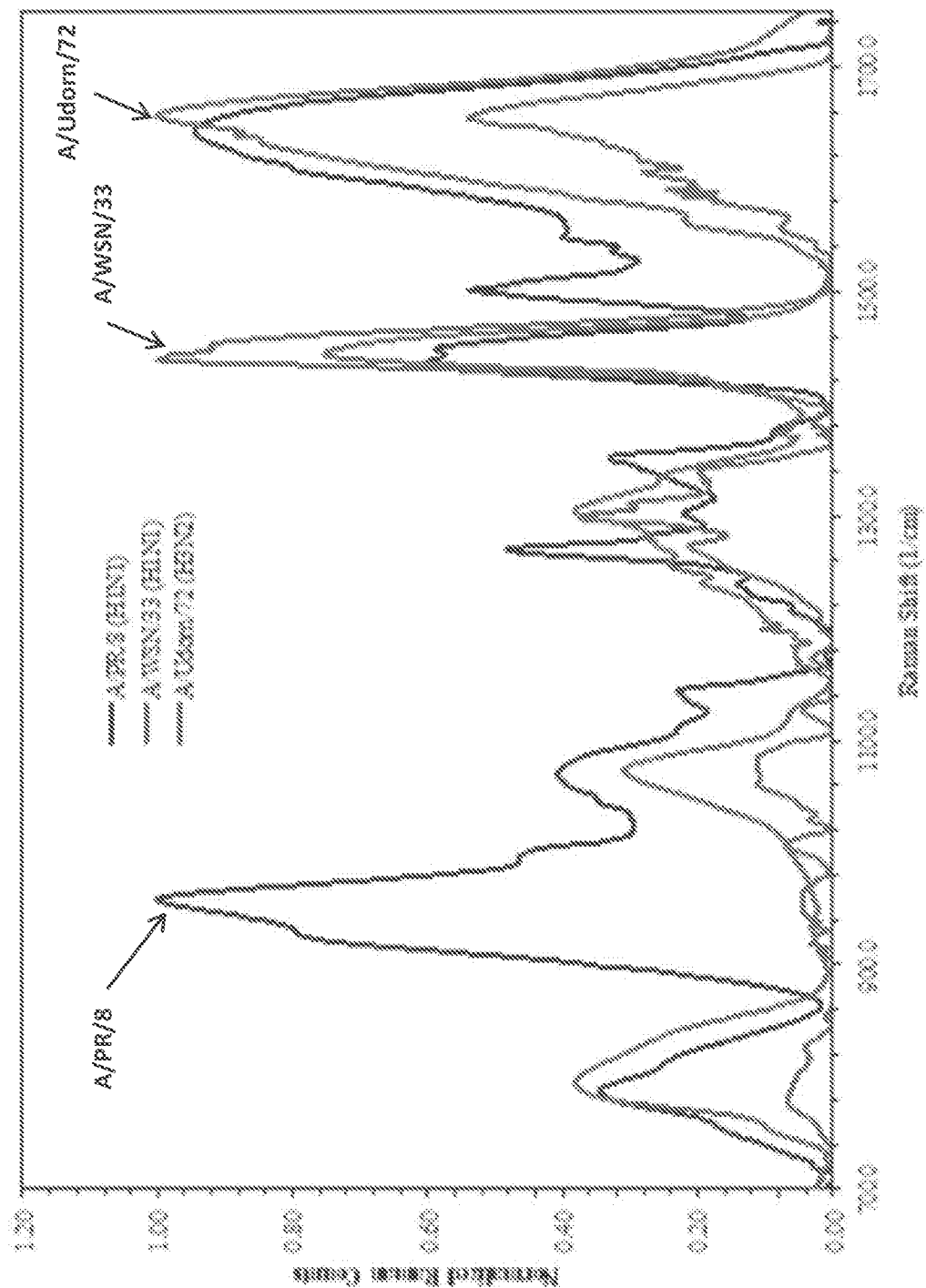
FIG. 9 illustrates spectral peaks for the three influenza virus at Raman shifts between 700 and 1700 $cm^{-1}$.

The classification results show that 94.5% of cross-validated grouped cases correctly classified with 95.8% of the *Staphylococcus* group, and 91.3% of the non-*Staphylococcus* group (*Cory* and *Bacillus*) correctly classifying. These results indicate that the regions of 640-740 cm$^{-1}$, 1200-1265 cm-1 have potential for bacteria identification. To test the model further, nasal swab samples inoculated with MRSA 1R, MRSA 2R, MSSA 1S or *S. epidermidis* were input into the analysis as unknowns. 100% of the cases correctly classified as *Staphylococcus*. Further, the mean spectra of the *Staphylococcus* species and strains show clear distinction in these regions as best seen in FIGS. 8 and 9.

Figure 4:
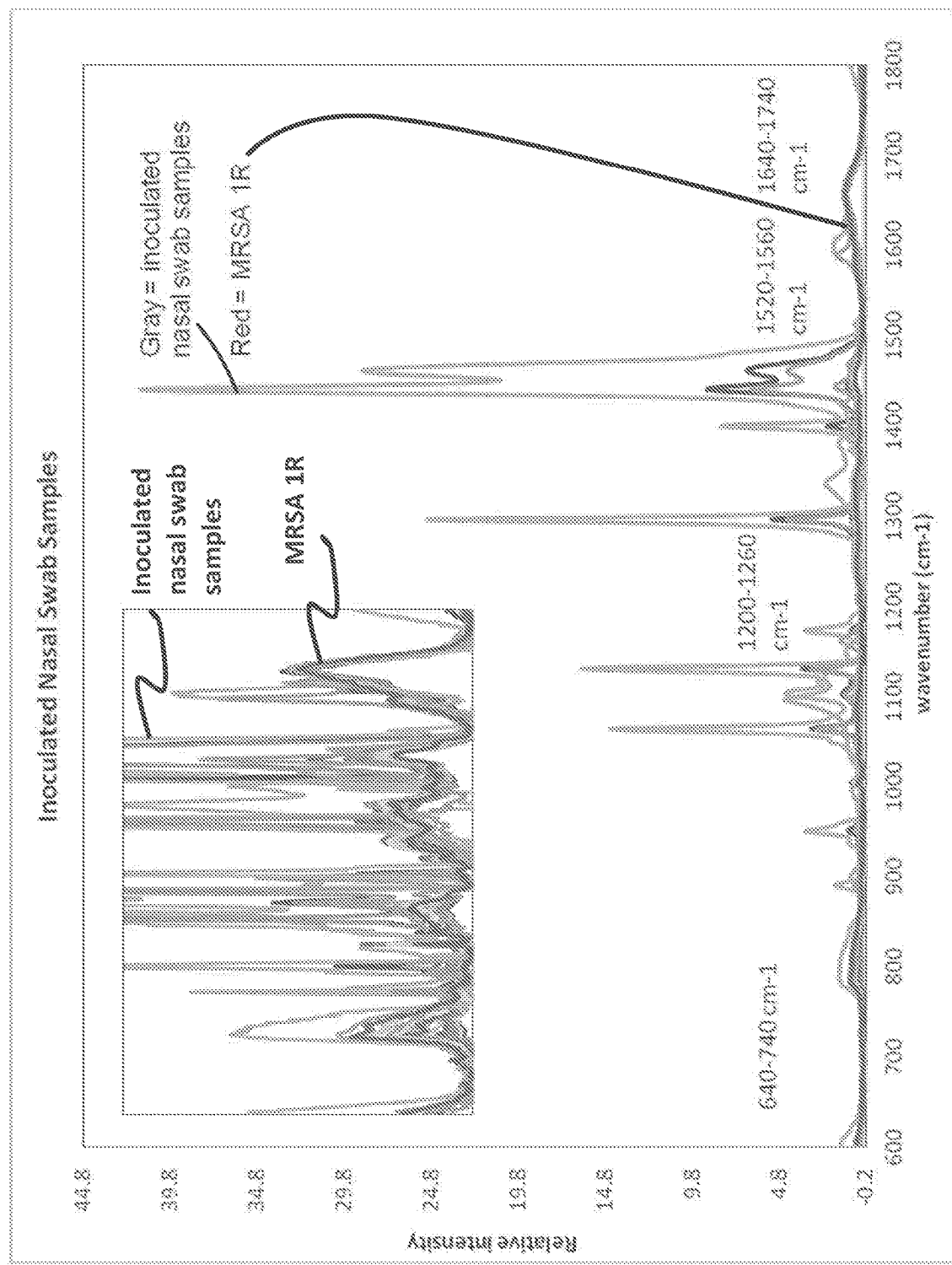
FIG. 4 illustrates a comparison of mean spectra for inoculated nasal swab samples (light) and MRSA 1R (dark)

The preliminary studies detailed above have shown a high confidence level that staph in general can be identified with 5 or less Raman spectral regions. In one embodiment of the invention, the system is designed to acquire Raman measurements in the presence of confounding factors. Measurements will be made directly in the nasal vestibule. The spectral regions of 640-740 cm-1, 1200-1265 cm-1, 1640-1740 cm-1 have minimal spectral components due to confounding factors and show utility for this application. In another embodiment, the otoscope contains a nasal aspirator allowing the sample to be drawn into the end effector of the otoscope through an internal filter. This filter in procedure will reduce the signal from background interference. The spectral bands for this configuration are shown in FIG. 4.

Figure 7:
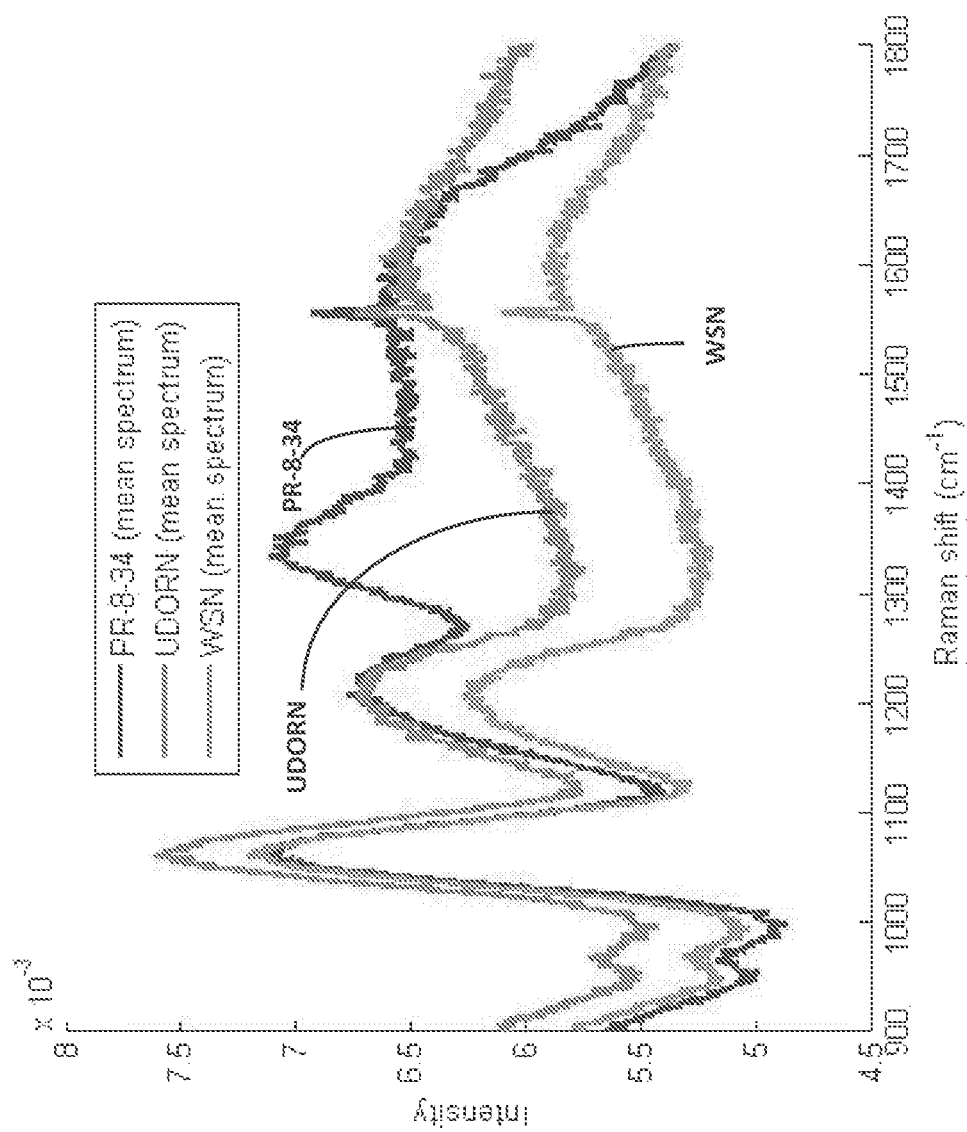
FIG. 7 illustrates a sample of the Raman spectra collected for three influenza virus.

An analysis for identifying influenza virus is done using a similar classification scheme. Raman spectra have been obtained for several purified influenza viruses in phosphate buffer solution using hand held micro Raman spectrometer at an excitation wavelength of 514.5 nm fitted with a fluidic probe as further described herein. An excitation wavelength of 514.5 nm, resulted in a significant fluorescence signal from the samples. However, Raman peaks associated with the target viruses were sufficiently strong to be detectable from the background fluorescent signal. A sample of the Raman spectra collected for three influenza virus examined are shown in FIG. 7. The three strains of influenza for which preliminary results are shown are as follows: A/PR/8 and A/WSN/33 both being of the H1N1 serotype and A/Udorn/72 of the H3N2 serotype.

The results confirm that Raman spectra can be obtained for influenza virus. In addition to confirming the utility of Raman for the investigation of influenza viruses, the data collected confirms that a number of Raman peaks exist for identification purposes. A comparison of the Raman spectra for A/PR/8 and A/WSN/33 shows a sufficient difference in the spectra, which provides distinguishing characteristics between viruses with the same serotype. The Raman spectra of all three viruses in FIG. 8 show a clear triplet of peaks at Raman shift between 2850 and 2950 cm$^{-1}$. These peaks are clearly present on all influenza viruses that we have been examined to date.

Figure 10:
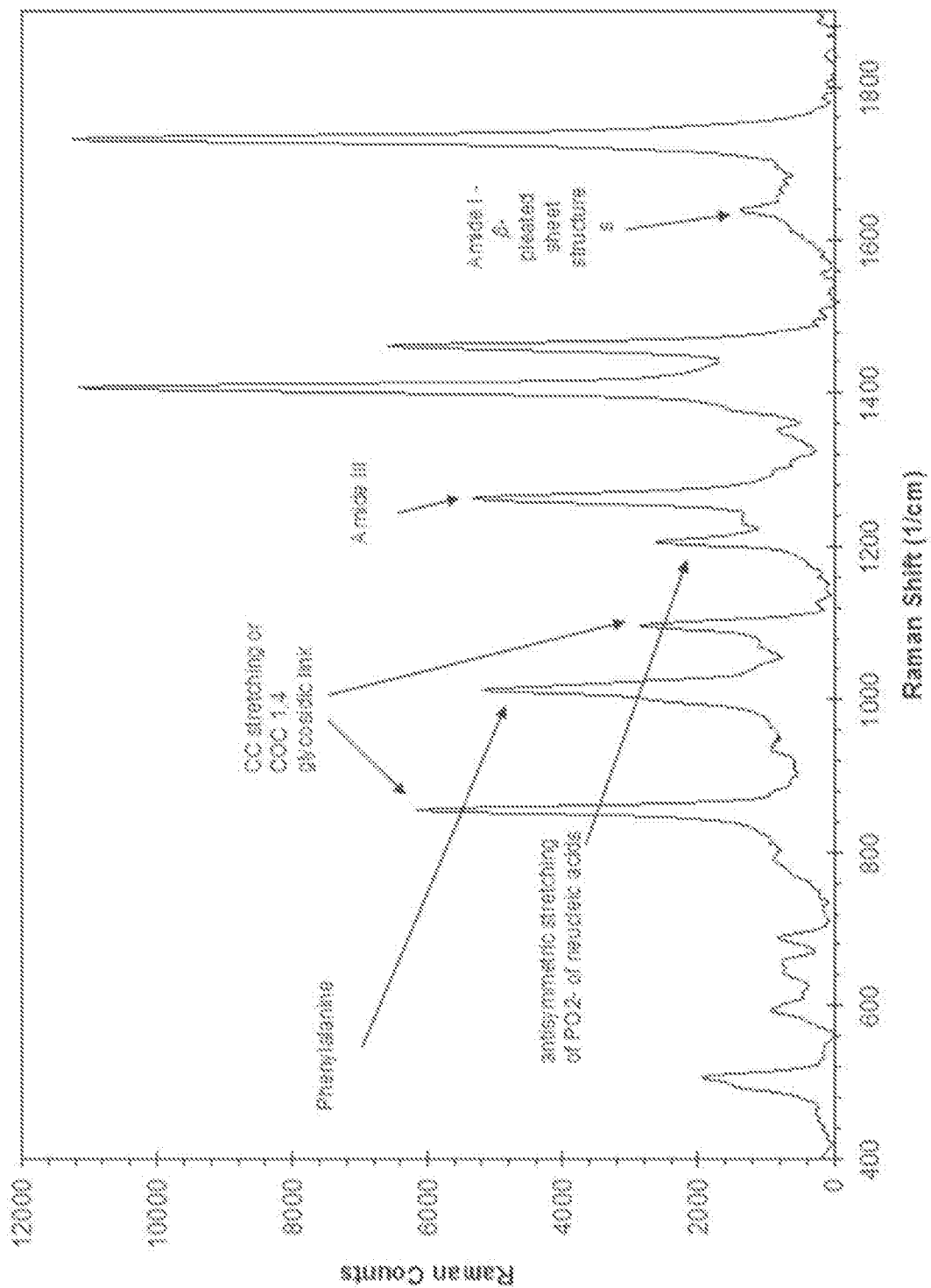
FIG. 10 illustrates the spectra of immobilized influenza utilizing background subtraction techniques.

This sample data clearly provides virus detection in general as compared to spectrum from other biological entities. At Raman shifts of approximately 700 to 1700 cm$^{-1}$, as shown in FIG. 9, a large number of distinct peaks are observed for all virus samples. While many of these peaks are common to all viruses tested, a close examination shows that the relative heights of the specific peaks as well as shifts in the position of some peaks differ with each virus strain. It is these peak ratios and shifts that are utilized to distinguish the various strains from one another. To increase the sensitivity and data characteristics of influenza, FIG. 10, shows the spectra of immobilized influenza utilizing background subtraction techniques. The spectral bands clearly identify the distinguishing pleated sheet structure amide I group as well as distinct carbon-carbon nucleic acids and other amide groups. These results clearly indicate influenza distinguishing abilities for Raman spectroscopy identification. The improvements in sensitivity and an increase in resolution in the described system will help in identifying and distinguishing differences in this region.

Figure 11:
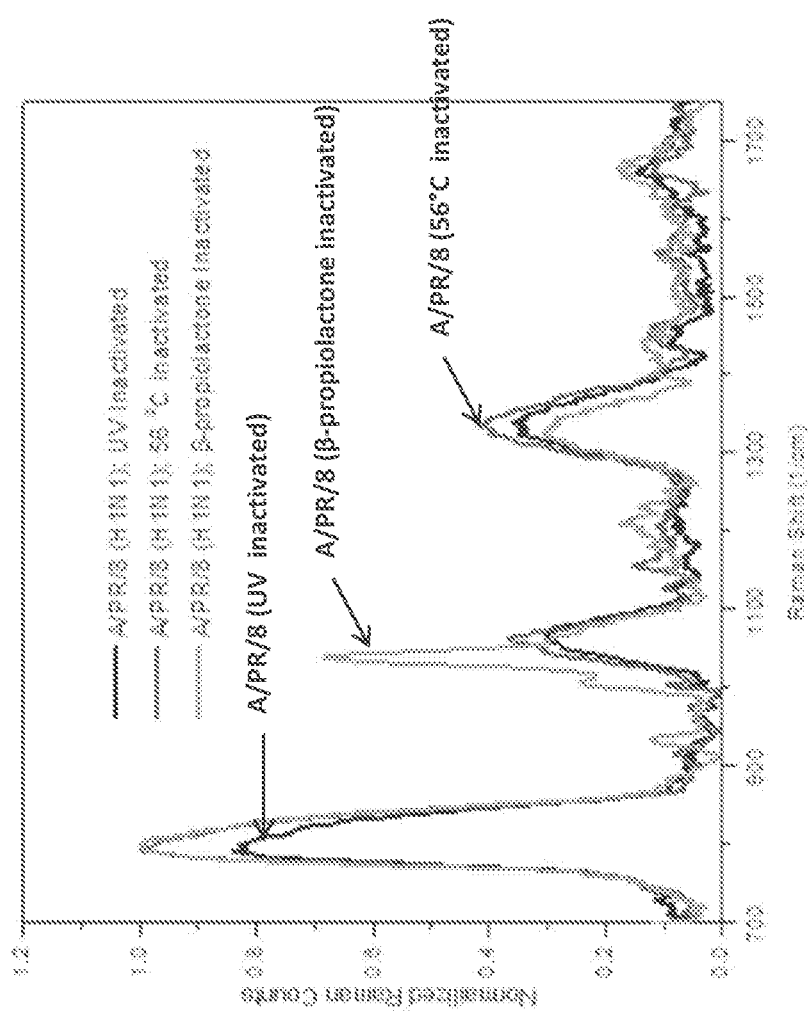
FIG. 11 illustrates spectra of an influenza virus which has been deactivated using different deactivation procedures including UV, thermal and chemical treatment.

The present disclosure further enables an analysis for distinguishing a live (active) virus from a dead (inactivated) virus. For example, results from sampling inactivated dried samples of A/PR/8 (H1N1) serotype influenza run at an excitation wavelength of 785 nm revealed difference in the Raman spectra of the virus based on the inactivation method utilized. The present disclosure has heretofore focused on active pathogen samples; however, preliminary results of testing the apparatus and methods described herein showed the Raman spectral data could be used to deactivation effects of the virus. In order to determine the deactivation effects of the virus, a sample of A/PR/8 was deactivated by three distinct methods: UV, heat, and chemical deactivation. When these samples were examined at an excitation wavelength of 785 nm, clear difference in the Raman spectra of the sample that was chemically deactivate were observed as can be seen in FIG. 11. This difference is most obvious in the shift of the peak from 1080 to 1040 cm$^{-1}$, but can also be seen in the minor shift of the peak located near 1340 cm$^{-1}$. Minor difference also exists between the UV and heat deactivated influenza samples, but indicates the sensitivity to change in the analysis. This information is useful for the identifying changes or mutations in the target virus. For example, FIG. 7 shows a significant portion of the mean Raman spectra of APR8/34 (H1N1), A/WSN/32 (H1N1), and A/Udorn/72 (H3N2) after preprocessing. Approximately 12 spectra averaged of each pathogen were averaged and the classification results are reproduced in Table 4 below.

TABLE 4

|  |  |  | Predicted Group Membership | | | |
| --- | --- | --- | --- | --- | --- | --- |
|  | Virus Type |  | WSN | PR-8-34 | UDORN | Total |
| Original | Count | WSN | 11 | 1 | 0 | 12 |
|  | dimension 2 | PR-8-34 | 0 | 8 | 0 | 8 |
|  |  | UDORN | 0 | 0 | 12 | 12 |
|  | % | WSN | 91.7 | 8.3 | .0 | 100.0 |
|  | dimension 2 | PR-8-34 | .0 | 100.0 | .0 | 100.0 |
|  |  | UDORN | .0 | .0 | 100.0 | 100.0 |

Example embodiments of a hand held micro Raman based detection instrument will now be described more fully with reference to FIGS. 12-24 of the accompanying drawings. Example embodiments are provided so that this disclosure will be thorough, and will fully convey the scope of this disclosure to those who are skilled in the art. Specific details may be set forth to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known structures, and well-known technologies are not described in detail.

The terminology used herein is for the purpose of describing particular example embodiments only and is not intended to be limiting. As used herein, the singular forms "a," "an," and "the" may include the plural forms as well, unless the context clearly indicates otherwise. The terms "comprises," "comprising," "including," and "having," are inclusive and therefore specify the presence of recited structure(s) or step(s); for example, the stated features, integers, steps, operations, groups elements, and/or components, but do not preclude the presence or addition of additional structure(s) or step(s) thereof. The methods, steps, processes, and operations described herein are not to be construed as necessarily requiring performance in the stated or any particular order discussed or illustrated, unless specifically identified as an order of performance. It is also to be understood that additional, alternative or equivalent steps may be employed.

When structure is referred to as being "on," "engaged to," "connected to," or "coupled to" other structure, it may be directly or indirectly (i.e., via intervening structure) on, engaged, connected or coupled to the other structure. In contrast, when structure is referred to as being "directly on," "directly engaged to," "directly connected to," or "directly coupled to" the other structure, there may be no intervening structure present. Other words used to describe the relationship between elements should be interpreted in a like fashion (e.g., "between" versus "directly between," "adjacent" versus "directly adjacent"). As used herein, the term "and/or" includes any and all combinations of one or more of the associated referenced items.

Terms of degree (e.g., first, second, third) which are used herein to describe various structure or steps are not intended to be limiting. These terms are used to distinguish one structure or step from other structure or steps, and do not imply a sequence or order unless clearly indicated by the context of their usage. Thus, a first structure or step similarly may be termed a second structure or step without departing from the teachings of the example embodiments. Likewise, spatially relative terms (e.g., "inner," "outer," "beneath," "below," "lower," "above," "upper") which are used herein to describe the relative special relationship of one structure or step to other structure or step(s) may encompass orientations of the device or its operation that are different than depicted in the figures. For example, if a figure is turned over, structure described as "below" or "beneath" other structure would then be oriented "above" the other structure without materially affecting its special relationship or operation. The structure may be otherwise oriented (e.g. rotated 90 degrees or at other orientations) and the spatially relative descriptors used herein interpreted accordingly.

Figure 12:
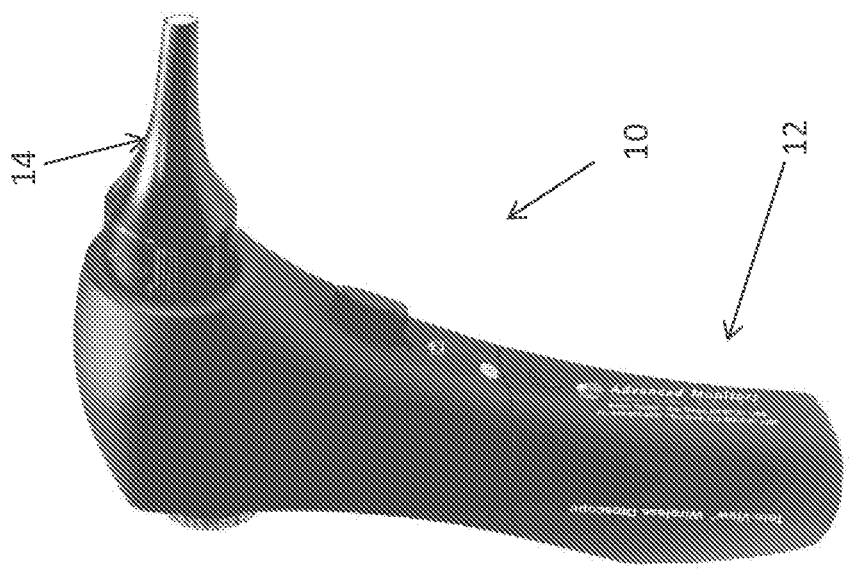
FIG. 12 illustrates an exemplary form factor of the hand held micro-Raman based detection instrument.

With reference now to FIG. 12, an exemplary form factor (e.g, Tele-View® Wireless Otoscope by Advanced Monitors Corp.) for the hand held Raman spectroscopy based system 10 is shown and which includes a miniature laser package and optics. The hand held system may be configured as an otoscope for testing in ears, nose and throat, as an ophthalmoscope for testing in the eyes or, more generally, as a hand held spectroscope for testing wounds sites, food or inanimate surfaces. Functional components of the system components include a hand held form factor housing 12 and, a disposable interrogation tip or end effector 14 that is used for nasal interrogation. The system can be used with three types of end effectors—one for direct nasal interrogation, one with vacuum suction and filter, and one with proximity optics for wound interrogation. Other components not shown in FIG. 12 but illustrated and described hereinafter include optical sampling head having a hybrid micro mirror, an integrated micro CCD or CMOS imager with ultra-high resolution narrow range spatially graded filter (takes the place of a large delicate spectrometer), signal processing and identification algorithms for signal conditioning and target detection.

Figure 13:
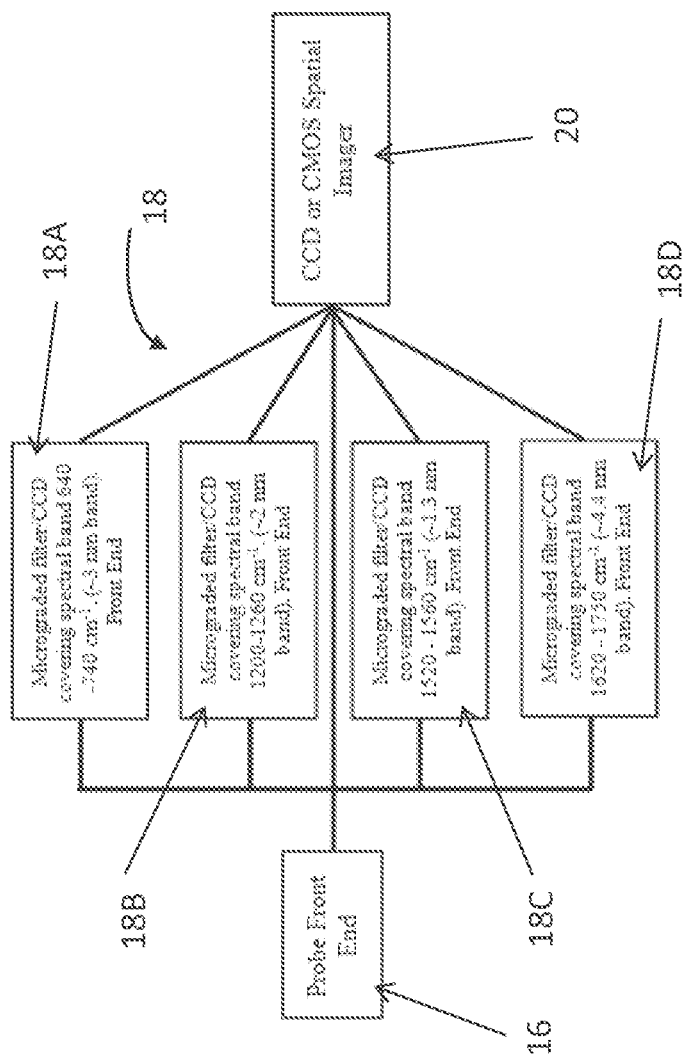
FIG. 13 illustrates the functional characteristics of the spectroscope shown in FIG. 12.

A key to developing a hand-held Raman spectroscopy based device is the development of analysis protocols that allow for target identification and classification. Spectral analyses from discrete Raman bands that distinguish a targeted substance from background interference form the basis of this development. These discrete bands are used to develop learning algorithms that serve as a basis for detection and identification. A diagram of the functionality of hand-held device is schematically illustrated in FIG. 13 to include a probe front end 16, a set of micro-graded filters 18 and an imager 20. The set of micro-graded filters are designed for filtering at the discrete band, e.g. filters 18A-18D. As presently preferred, Filter 18A is a micro-graded filter covering spectral band 640-740 $cm^{-1}$ (~3 nm band), filter 18B is a micro-graded filter covering spectral band 1200-1260 $cm^{-1}$ (~2 nm band), filter 18C is a micro-graded filter covering spectral band 1520-1560 $cm^{-1}$ (~1.3 nm band), and filter 18D is a micro-graded filter covering spectral band 1620-1750 $cm^{-1}$ (~4.4 nm band). It should be noted for an excitation beam at 532 nm, filter 18A filters a band in the range of 550.57-553.80 nm, filter 18B filters a band in the range of 568.28-570.22 nm, filter 18C filters a band in the range of 578.80-580.18 nm, and filter 18D filters a band in the range of 582.17-586.61 nm. The imager 20 may be a CCD, a CMOS or other similar digital imaging devices.

This point-of-care (POC) diagnostic technology is relatively low cost and demonstrates feasibility for use in the resource-limited settings and triage settings to non-clinical utilities. The device allows for sample collection (with disposable nasal end effector on the device), processing and result read-out in the same area, without the need to send samples to a central collection point for processing or testing. It requires no sample manipulation and provides safe-containment of bio-hazardous material with routine disposal of the disposable tip. Output is provided in a visual format, without ambiguity, and includes a full process negative and internal positive control. Read-outs are available as inputs into medical management protocols. The system may also include an integrated barcoding system as a way of connecting a sample taken perhaps hours earlier to the individual who provided that sample.

As noted above, the device is designed for operation in non-ideal conditions, which are expected for a field or point of care deployable instrument. This includes an ability to operate under temperature extremes between 0 and 45 degree Celsius. If the design is such that version capable of operating from −25 to +50 degrees Celsius could be produced, but may require heaters to prevent freezing that could impact battery life. The device is also designed to be water and dirt resistant to allow the devices to operate under non-ideal conditions. Only the disposable end effector is exposed to the patient, thus no sterilization or cleaning of the device will be required between uses. The exposed surfaces of the device may be fabricated with antimicrobial or bacterium-resistant material.

The device, as an option, may also utilize existing bar code bracelets if already assigned at the point-of-care facility or site. The device includes a small low-power processor to operate the device, collect and analyze data, and store results. The device includes a USB controller to allow for the downloading of data from the POC device's internal storage to external devices, as well as real time display. The device on an auxiliary monitor may also include standard wireless/cellular cards if desired. The device utilizes an externally accessible, readily swappable, rechargeable battery pack for power.

A schematic representation of the components of the hand-held Raman spectroscopy based device 10 is shown in FIG. 14. In this example, radiation from laser 22 is directed through a laser line filter 24, which transmits laser light while suppressing ambient light, to a 45° beam splitter 26. The beam splitter 26 reflects the laser light through the disposable end effector 14 to the samples where it interacts with the sample producing a Raman shifted signal. Light is collected from the sample at a 180-degree geometry and is transmitted through the beam splitter 26 and laser blocking filter 28. The laser blocking filter further prevents undesired laser light from reaching the detector 30.

The Raman shifted signal then impinges upon a beam expander 32 (for example a simple beam expander 32A, 32B as shown in FIGS. 18A and 18B, respectively) that increase the diameter of a collimated input beam to a larger collimated output beam. The particular configuration and shape of the beam expander optics may be changed, such as off axis parabolic reflection, to make the beam expander more efficient and easily packaged within the device. The optical signals of the output beam are converted to electrical signals by an imager 30 with ultra-high resolution narrow range spatially graded filter 34 for processing. Filter 34 preferably includes a set of micro-graded filters 34A-34D as described in reference to FIG. 13.

The disposable end effector 14 schematically illustrated in FIG. 15 is an attachment that interacts with the patient either inserted into the nasal passage or in proximity to a wound or infection situs. For direct nasal or wound interrogation, a lens 36 is integrated at tip of the end effector to allow laser light be focused onto the specimens and Raman scattered light to be collected. As shown in FIG. 16, a modified end effector 14' is used when sample filtration is required. The end effector 14' will connect to a vacuum source 38 allowing the sample to be drawn into the end effector body through an internal filter 40. In one embodiment, the device may be fitted with a small vacuum pump which functions as the vacuum source 38 removes gas molecules (air) from a sealed volume, denoted by the dashed line in FIG. 14, in order to leave behind a partial vacuum. The vacuum will draw the sample into the end effector 14'. Raman measurement takes place at an optical window 42 fabricated out of an optically transparent material such as quartz. The optical window 42 is located concentrically within a mesh 44 and a seal 46 formed on an end of the end effector 14' opposite the filter 40. Filtering the sample will reduce the signal from background interference by trapping large debris allowing bacteria or virus to pass through for measurement.

The system is configured to deliver and collect light from the sample using an open beam path. Lens tubes 24, 38 are utilized to isolate the optical path and reduce stray light.

The end effectors 14, 14' shown are disposable specula that detachably connects to the head 48 of the device 10 with, for example a twist lock connection to allow for precise optical alignment and ease of end effector (tip) removal. The end effector connectors may be equipped with or without a focusing lens. For vacuum suction application, the connector will house a lens 36 to allow laser light be focused onto the sample and Raman scattered light to be collected. For wound and direct nasal interrogation, the lens will be absent. The specula is designed as a single use component that is detached from the device head 48 and disposed in accordance with medical waste disposal procedures.

For this system, the incident beam and collected signal light share a common path such that a 45° beam splitter 26 is used to reflect the laser light through the optics to the sample while efficiently transmitting the returning Raman-shifted signal light. A laser-blocking filter 24 at normal incidence is used ahead of the dispersion element 26 to completely block the undesired laser light. The diameter of a collimated input beam is increased with a beam expander 32 to a larger collimated output beam. With reference to FIGS. 13, 19A and 19B, a set of ultra-high resolution micro-filter quadrants 34A-34D are arranged in front of the imaging detector 30 and provide specific wavenumber or spectral band filtering by the discrete waveband analysis. Each quadrant 34A-34D allows for discrete spectral band detection with each micro-filter providing specific wavenumber detection for spectral analysis. The quadrants 34A-34D may be arranged symmetrically about the x and y axes as shown in FIG. 19A, or arranged in vertical bands as shown in FIG. 19B. The image sensor 30 converts the optical signals, into electrical signals. The imaging sensor 30 can be an integrated CCD or CMOS or the like.

The unique micro optical filters provide a narrow range of spatially graded filter, which span the narrow spectral region covering a specific Raman Spectral peak or narrow region of closely neighboring peaks. Commercial graded filters do not have sufficient resolution to achieve 1 cm-1 spatial resolution. The spectral wavelength is transformed to an imaging array position/intensity reading that provides a reconstruction of the spectral peaks of interest. The method of fabrication is a graded Indium Aluminum Nitride (InAlN) alloy that can provide spectral filtering by band gap engineering at any region between 1 eV and 6 eV band gap or 1240 nm to 206 nm. A hollow cathode based low energy plasma deposition is used to deposit the nitride alloy. Deposition is controlled by a sliding substrate window coordinated with a change in Indium deposition rate creating the graded optical coating.

A narrow line width laser 22 packaged in a module with integral drive electronics is used for Raman excitation. The wavelength and laser power is chosen based upon the application. The laser is able to be used as an open beam source or be coupled to an optical waveguide.

The spectrometer subsystem includes an electronic subsystem as well as an internal lithium-ion battery pack 52 to provide power to the system and allow for field-portable use. The system 10 is powered from either its internal battery pack or via an external charger/power adapter. The device 10 may have a provision for monitoring battery life and charge status. The device 10 may be designed with a USB controller (not shown) to allow for the downloading of data from the internal storage of the point of care (POC) device to external devices as well as a real time display (not shown). In the form of a compact LCD panel. The device may also be built to accommodate standard wireless/cellular communication if desired. The spectrometer electronic subsystem 50 utilizes a dedicated micro-controller to read the spectrum measured with the imaging sensor 30, performs the basic processing of the image data, and transmits that information to a display, PC or other similar interface. As previously noted, the device 10 may be fitted with a small vacuum 38 for pump to work in conjunction with the disposable end effector 14' with filter for vacuum suction application.

In another embodiment, an device 110 is designed as a Raman probe with optic connection to a portable detection system 112 as shown in FIGS. 20 and 24. The device 110 is designed to deliver laser light to the sample and collect Raman scatter. To accomplish this, the device 110 is configured with waveguides, lenses, and filters that function to transmit the Raman scatter from the sample to the detection system for spectral analysis in a manner similar to that described with respect to device 10.

The detection system 112 is a portable unit approximately 24 cm×10 cm×3 cm in size (6"×4"×1"). Key components include a laser 114 optically coupled to the device 110 for Raman excitation, and a spectrograph subunit 114 optically coupled to the device 110 for the measurement of Raman radiation intensity as a function of wavelength. A spectrograph subunit 116 indicated by the dashed box in FIG. 20 can be configured as, but is not limited to: a grating spectrometer, a prism spectrometer, or an interferometer. The detection system 112 will also incorporate a micro controller 118 for signal processing and identification algorithms for signal conditioning and target detection, as well as support a user friendly graphical display that acts as the human-machine interface. A color LCD display will have sufficient resolution to display use instructions, as well as test results in text output for go/no-go classification, and to graphically display a spectra. A simple menu structure with large pushbutton icons make operation of the device straight forward and user friendly.

As shown in FIGS. 20 and 24 the spectroscope subunit 116 is configured as a Czerny-Turner spectrometer. Radiation from laser 114 is directed through a flexible optical waveguide (fiber) 120 to the device 110 and is transmitted through a laser line filter 122 and disposable end effector 124 to the samples. The light interacts with the sample producing a Raman shifted signal which is collected at 180-degree geometry. The collected light is transmitted thought a laser blocking filter 122 and coupled into a flexible optical waveguide (fiber) 126. The laser blocking filter 122 prevents undesired laser light from reaching the detector. The Raman shifted signal is directed through the optical waveguide (fibers) 126 to the spectroscope subunit 116 of the detection system 112. Light entering the subunit 116 is reflected off of the collimating mirror 128 and is directed onto the diffraction grating 130 which separates incident polychromatic light into constituent wavelength components. The diffracted light is directed to a focusing mirror 132 onto a detector 134 which converts optical to electrical signals for processing.

As presently preferred, the disposable end effector 124 is a disposable specula that interacts with the patient either inserted into the nasal passage or in proximity to a wound or infection sight. The end effector design is similar to that described in FIGS. 15-17.

Further details of the optical train for the device 110 are illustrated in FIGS. 21-23D. Light from the laser 114 is coupled into the excitation fibers 120e of the probe as shown in FIG. 19. As best seen in FIG. 22A, the excitation fibers 120e form part of the fiber bundle 120 which are concentrically arranged around the collection fiber 120c. In a preferred embodiment, the collection fiber 120c has a diameter approximately four times larger than the diameter of the excitation fiber 120e. A high rejection filter (laser line filter) 122A at the output of these fibers is used to remove Raman bands arising from the silica core, thus allowing only the laser light to be transmitted to the sample. Hollow core Photonic crystal fibers are used as excitation fibers in order to reduce/eliminate the need for filtering.

Off axis parabolic mirrors 136, located beneath the excitation fibers 120 collimate and direct the beams to a 45 degree cone lens 138. FIG. 22C illustrate an excitation beam transmitted from the excitation fibers 120e and impinging on the face of the cone lens 138. As presently preferred, the height of the cone lens 138 is approximate twice the diameter of the excitation fiber 120e as best seen in FIG. 22B. This lens 138 has dielectric coated faces that allow the laser light to be reflected and the Raman scatter to be transmitted. In particular, the outside surface of the lens 138 is coated with a dielectric to reflect laser light and pass Stokes scattered light. The reflected laser light is directed toward the sample surface and focused with a convex lens. When the lens is absent, collimated light is output from the probe. Light scattered from a sample is collected 180 degrees relative to the direction of the laser beam. It is directed through the cone lens 138 which allows only the Raman scattered light to be coupled into the collection fiber 126.

Two key elements of this design are the off axis parabolic mirror 136 system and the 45 degree cone lens 138. As best seen in FIG. 23B, the off axis parabolic mirror is an annular or doughnut shaped optic that has eight conic depressions or dimples 140 on its surface. Each of the eight dimples 140 forms a 90 degree parabolic mirror with its focal point at a designated excitation fiber 120e. As shown in FIGS. 21, 22B, 22C, 23C and 23D, the cone lens 138 is a hollow hexagonal optical element whose faces are at a 45 degree angle. The lens 138 has a dielectric coating enabling it to act as a long pass filter (reflecting laser light and transmitting the Raman scatter).

Other features incorporation into the system includes: a strain relief boot 142 which provide strain relief to fiber cables, and exhibit a high degree of flexibility. A first connector 144 secures the excitation fiber (waveguide) of the device 110 to the laser 114. A second connector 146 secures the Raman collection fiber (waveguide) of the device 110 to the spectrograph subunit 116. A narrow line width laser 114 is packaged in a module with integral drive electronics for Raman excitation. The wavelength and laser power is selected based upon the application and target identification. The laser is coupled to an optical fiber or waveguide with use of a third connector.

The second fiber connector 146 secures the input fiber 126 (or waveguide) to the spectrograph subunit 116. Light from the input fiber (or waveguide) enters the detection system through this connector. Behind the connector, a slit (not shown) having a dark piece of material containing a rectangular aperture may be utilized. The collimating mirror 128 focuses light entering the spectrometer portion of the detection system towards the grating 130. Diffraction grating 130 diffracts light from the collimating mirror 128 and directs the diffracted light onto the focusing mirror 132. The dispersive element 130 separates incident polychromatic light into constituent wavelength components and can be a grating or prism or a like. Focusing mirror 132 receives light reflected from the grating 130 and focuses the light onto the CCD Detector 134. CCD detector 134 collects the light received from the focusing mirror 132 and converts the optical signal to a digital signal. Each pixel on the CCD Detector corresponds to the wavelength of light that strikes it, creating a digital response signal.

As noted above, the detection system 112 includes an internal lithium-ion battery pack (not shown) to provide power to the system and allow for field-portable use. The system can be run from either its internal battery pack or via an external charger/power adapter. The device 112 will have a provision for monitoring battery life and charge status. The detection system 112 may include an electronic sub-system which includes a PC-based processor 148, spectrometer 116, vacuum pump and valve controller (not shown), pressure sensors (not shown), and interlocks. PC-based processor is used to perform all of the computation and coupled to an LCD display 150 with a touch screen and/or perimeter function buttons 152 to handle menu selection. The spectrometer subsystem 112 utilizes a dedicated micro-controller 118 to read the CCD array, perform basic processing on the image data, then transmit that information to the PC using a USB or other similar interface.

With reference now to FIG. 25, a flow chart 210 illustrating the detection process is provided. In particular, a hand-held Raman spectroscopic device as described above is operated to transmit a coherent light beam from the excitation laser onto a sample. The imaging sensor detects radiation from the filtered Raman-shifted sample signal (block 212) and generates image data representative thereof (block 214). The image data is then analyzed (block 216) and the spectral features at discrete spectral bands are examined to detect the presence of a target pathogen (block 218). If no target pathogenic features are found, the device displays and/or reports a negative result for the presence of the target pathogen (block 220).

If target pathogenic features are found, these features are compared with baseline Raman spectra (block 222). Algorithms and classification coefficients are computed based on the baseline spectra (block 224). Typing of the target pathogenic features is done in a hierarchical approach and classification is assigned as the comparison moves down the hierarchy (block 226). If a positive database match is identified, the device displays and/or reports a positive result for the presence of the target pathogen (block 228). If a positive database match is not identified, the probability of the target pathogen's identity or membership within a particular group of interest may be computed and displayed or reported (block 230).

A robust portable Raman spectroscopy based system as detailed above has many anticipated benefits. The nonintrusive, nondestructive technique for nasal examination and wound interrogation provides rapid and cost effective screening of a wide range of protein-based compounds including bacteria, virus, drugs, and tissue abnormalities. The method requires little or no sample preparation, reducing the need for storage of consumables. In addition, the ease of use and non-contact sampling make the device a valuable tool for point of care investigations.

The device is a reagentless automated near real time point of care detection system that can enable healthcare providers to render better patient management and optimize clinical outcomes. Since the sensor can be developed to analyze bacteria, virus, drugs, and tissue, it can be promoted to a variety of market segments that include: primary care physicians, and drug stores.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A Raman spectroscopic system comprising:
an excitation light source to radiate coherent light onto a sample;
a collector to collect a Raman signal from the sample;
a beam collimator to collimate the collected Raman signal and generate a collimated Raman signal;
an optical filter to filter the collimated Raman signal, wherein
the optical filter comprises a plurality of micro-filters arranged co-planarly and spatially adjacent to each other, and
each of the micro-filters is configured to transmit a different spectral band of the collimated Raman signal;
a dispersive element to disperse the collimated Raman signal and direct the dispersed collimated Raman signal to the optical filter; and
an imaging sensor array comprising a plurality of detection areas to separately detect each of a plurality of different spectral bands transmitted from each of the micro-filters.

2. The system of claim 1, wherein the different spectral bands comprise at least one of 640-740 $cm^{-1}$, 1040-1080 $cm^{-1}$, 1200-1265 $cm^{-1}$, 1320-1340$^{-1}$, 1520-1560 $cm^{-1}$, 1620-1750 $cm^{-1}$, and 2850-2950 $cm^{-1}$.

3. The system of claim 2, wherein the different spectral bands comprise at least two of 640-740 $cm^{-1}$, 1200-1265 $cm^{-1}$, 1520-1560 $cm^{-1}$, and 1620-1750 $cm^{-1}$.

4. The system of claim 1, wherein the micro-filters each have a spectral resolution of 1 $cm^{-1}$.

5. The system of claim 1, wherein the micro-filters are micro-graded filters.

6. The system of claim 1, wherein the micro-filters each comprise a graded Indium Aluminum Nitride (InAlN) alloy coating.

7. A method for distinguishing an active pathogen from an inactivated pathogen using Raman based spectroscopic analysis, the method comprising:
- radiating coherent light onto a sample;
- collecting a Raman signal from the sample;
- collimating the Raman signal;
- dispersing the collimated Raman signal;
- directing the dispersed Raman signal to an optical filter;
- detecting the filtered Raman signal by an imaging sensor array, the imaging sensor array comprising a plurality of detection areas to separately detect each of a plurality of different spectral bands of the filtered Raman signal;
- analyzing the Raman signal for the presence of a pathogen; and
- analyzing the Raman signal for a Raman peak spectral shift indicative of a change in activity of the pathogen.

8. The method of claim 7, further comprising analyzing the Raman signal for the Raman peak spectral shift that is in a spectral band selected from 640-740 $cm^{-1}$, 1040-1080 $cm^{-1}$, 1200-1265 $cm^{-1}$, 1320-1340 $cm^{-1}$, 1520-1560 $cm^{-1}$, 1620-1750 $cm^{-1}$, and 2850-2950 $cm^{-1}$.

9. The method of claim 7, further comprising simultaneously filtering, by the optical filter, the dispersed Raman signal in a plurality of different spectral bands.

10. The method of claim 9, wherein the different spectral bands comprise at least one of 640-740 $cm^{-1}$, 1040-1080 $cm^{-1}$, 1200-1265 $cm^{-1}$, 1320-1340$^{-1}$, 1520-1560 $cm^{-1}$, 1620-1750 $cm^{-1}$, and 2850-2950 $cm^{-1}$.

11. The method of claim 10, wherein the different spectral bands comprise at least two of 640-740 $cm^{-1}$, 1200-1265 $cm^{-1}$, 1520-1560 $cm^{-1}$, and 1620-1750 $cm^{-1}$.

12. The method of claim 7, wherein the optical filter comprises a plurality of micro-filters arranged co-planarly and spatially adjacent to each other, and each of the micro-filters is configured to transmit a different spectral band of the dispersed Raman signal.

13. A method of making a graded optical filter, comprising:
- depositing an Indium Aluminum Nitride (InAlN) alloy coating on a substrate by hollow cathode-based low energy plasma deposition;
- sliding the substrate during the deposition; and
- changing Indium depositing rate to coordinate with sliding of the substrate to create a graded InAlN coating having a band gap between 1 eV and 6 eV.

14. The method of claim 13, wherein the graded optical filter comprises a plurality of micro-graded filters each having a different spectral band.

15. The method of claim 14, wherein the different spectral bands comprise at least one of 640-740 $cm^{-1}$, 1040-1080 $cm^{-1}$, 1200-1265 $cm^{-1}$, 1320-1340$^{-1}$, 1520-1560 $cm^{-1}$, 1620-1750 $cm^{-1}$, and 2850-2950 $cm^{-1}$.

16. The system of claim 10, wherein the different spectral bands comprise at least two of 640-740 $cm^{-1}$, 1200-1265 $cm^{-1}$, 1520-1560 $cm^{-1}$, and 1620-1750 $cm^{-1}$.

17. The method of claim 14, wherein the micro-filters each have a spectral resolution of 1 $cm^{-1}$.

* * * * *

UNITED STATES PATENT AND TRADEMARK OFFICE
CERTIFICATE OF CORRECTION

PATENT NO. : 11,236,379 B2
APPLICATION NO. : 16/284050
DATED : February 1, 2022
INVENTOR(S) : Gregory William Auner et al.

It is certified that error appears in the above-identified patent and that said Letters Patent is hereby corrected as shown below:

In the Claims

In Claim 2, Column 18, Line 56, "1320-1340$^{-1}$," should read --1320-1340 cm$^{-1}$,--.

In Claim 10, Column 19, Line 29, "1320-1340$^{-1}$," should read --1320-1340 cm$^{-1}$,--.

In Claim 15, Column 20, Line 23, "1320-1340$^{-1}$," should read --1320-1340 cm$^{-1}$,--.

Signed and Sealed this
Twelfth Day of July, 2022

Katherine Kelly Vidal
*Director of the United States Patent and Trademark Office*